(12) United States Patent
Meissner et al.

(10) Patent No.: US 6,852,728 B2
(45) Date of Patent: Feb. 8, 2005

(54) ANTICHOLINERGICS, PROCESSES FOR PREPARING THEM, AND PHARMACEUTICAL COMPOSITIONS CONTAINING THEM

(75) Inventors: Helmut Meissner, Ingelheim (DE); Gerd Morschhaeuser, Ingelheim (DE); Michael Paul Pieper, Ingelheim (DE); Gerald Pohl, Biberach (DE); Richard Reichl, Gau-Algesheim (DE); Georg Speck, Ingelheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 09/965,766

(22) Filed: Sep. 28, 2001

(65) Prior Publication Data

US 2002/0119991 A1 Aug. 29, 2002

Related U.S. Application Data

(60) Provisional application No. 60/249,350, filed on Nov. 16, 2000.

(30) Foreign Application Priority Data

Oct. 14, 2000  (DE) .......................................... 100 50 995

(51) Int. Cl.$^7$ ..................... A61K 31/46; C07D 451/10; C07D 451/00; A61P 11/06; A61P 13/06
(52) U.S. Cl. ..................... 514/291; 514/304; 546/91; 546/131; 546/130; 546/129
(58) Field of Search ................... 546/131, 91; 514/304, 514/291

(56) References Cited

U.S. PATENT DOCUMENTS

| | | | |
|---|---|---|---|
| 3,826,836 A | | 7/1974 | Buchel et al. |
| 4,042,700 A | | 8/1977 | Banholzer et al. |
| 4,608,377 A | | 8/1986 | Banholzer et al. |
| 4,783,534 A | | 11/1988 | Banholzer |
| 5,610,163 A | | 3/1997 | Banholzer et al. |
| 5,654,314 A | * | 8/1997 | Banholzer et al. .......... 514/291 |
| 5,770,738 A | * | 6/1998 | Banholzer et al. .......... 514/304 |
| 5,952,505 A | | 9/1999 | Banholzer |
| 5,977,115 A | | 11/1999 | Patane et al. |
| 6,486,321 B2 | | 11/2002 | Banholzer et al. |
| 6,506,900 B1 | | 1/2003 | Banholzer et al. |
| 6,706,726 B2 | * | 3/2004 | Meissner et al. .......... 514/291 |
| 2002/0115680 A1 | | 8/2002 | Meissner et al. |
| 2002/0133010 A1 | | 9/2002 | Banholzer et al. |
| 2003/0203928 A1 | | 10/2003 | Germeyer et al. |

FOREIGN PATENT DOCUMENTS

| | | |
|---|---|---|
| CH | 325296 | 1/1954 |
| DE | 1 232 157 | 5/1963 |
| DE | 25 40 633 | 4/1977 |
| EP | 0 513 533 A2 | 11/1992 |
| EP | 0 519 831 A1 | 12/1992 |
| JP | 06200202 | 7/1994 |
| WO | WO 92/16528 | 10/1992 |

OTHER PUBLICATIONS van Zwieten et al. Cardiovascular drugs and therapy/sponsored by the International Society of Cardiovascular Pharmacotherapy, 1995, 9(1): 159–67.*
Xu et al. Chemical & Pharmaceutical Bulletin, 1998, 46(2): 231–41.*
Emran AM et al. Chem. Views Imaging Cent., [Proc. Am. Chem. Soc. Symp.] (1995), Meeting Date 1993, 485–96. Editor(s): Emran AM. Publisher: Plenum, New York, NY.*
Zakharova NA et al. Sh. Org. Khim. (1967), 3 (6), 1128–36.*
Chemical Abstract—122:108910—JP 06200202, Murakami, et al JP 1991–176741.
XP–002205458—Cannon, Joseph G. ; Esters of Benzilic Acids and Congeners Having Potential Psychotomimetic Activity, Esters of Benzilic Acide, Jun. 1960, 959–962.

(List continued on next page.)

Primary Examiner—Evelyn Mei Huang
(74) Attorney, Agent, or Firm—Robert P. Raymond; Timothy X. Witkowski; Anthony P. Bottino

(57) ABSTRACT

A compound of formula 1

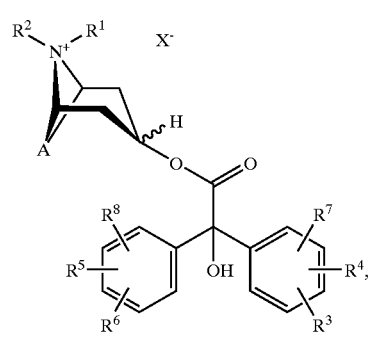

wherein:
A is a group selected from

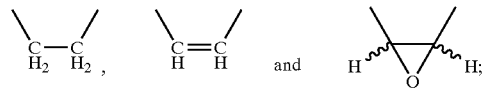

$X^-$ is an anion with a single negative charge;
$R^1$ and $R^2$ are each independently a $C_1$–$C_4$-alkyl optionally substituted with hydroxy or halogen; and
$R^3$, $R^4$, $R^5$, $R^6$, $R^7$, and $R^8$ are each independently hydrogen, $C_1$–$C_4$-alkyl, $C_1$–$C_4$-alkyloxy, hydroxy, $CF_3$, CN, $NO_2$, or halogen,
with the proviso that at least one of the groups $R^3$, $R^4$, $R^5$, $R^6$, $R^7$, and $R^8$ is not hydrogen, processes for preparing these compounds, pharmaceutical compositions containing these compounds, and their use as pharmaceutical compositions.

17 Claims, No Drawings

OTHER PUBLICATIONS

XP-002205554—Ohwada, T. et al; Superacid–Catalyzed Electrocyclization of Diphenylmethyl Cations to Fluorenes. Kinetic and Theoretical Revisit Supporting the Involvement of Ethylene Dications, J. Am Chem. Soc. 1998, 120, 4629–4637.

Chemical Abstract 1686—XP-002205460—Brown, B.T. et al; Morphactin–like activity of benzilate esters in *Arabidopsis thaliana*; Plant Growth Subst., Proc. Ints., Conf., 7th (1972) Meeting Date 1970, 318–23.

Chemical Abstract 1753—XP-002205413—Emran, Ali et al; Flourinated tropanyl esters for application with PET, Chem. Views Imaging Cent., (Proc. Am. Chem. Soc. Symp.) (1995) Meeting Date 1993, 485–96).

Chemical Abstract 1754—XP-002193560—Zahkarova, N. et al; Esters of tropine 1-(diethylamino)-2-propanol, and beta,-(diethylamino) ethanol ; Zh. Org. Khim. (1967), 3(6), 1128–36.

L. Sojak, et al: CGC–FTIR Characterization of Mononitro and Dinitro isomers from Nitration Mixtures of Methyl Arylacetates, Chem Papers 52(1)34–40 (1998).

L. Sojak, et al; Identification of the Isomers from mono– and dinitration of a–hydroxydiphenylacetic acid by capillary gas chromotography with Fourier transform Infrared and mass spectrometric detection, Journal of Chromatography A. 695 (1995) 57–64.

P. Buchwald and N. Bodor; Structure–based estimation of enzymatic hydrolysis rates and its application in computer aided retrometabolic drug design, Pharmazie 55 (2000) 3, p 210–217.

Chemical Abstracts vol. 79, 1973, p. 86 and 87.

Deutsches Patent—und Markenamt—Document (2001).

* cited by examiner

ANTICHOLINERGICS, PROCESSES FOR PREPARING THEM, AND PHARMACEUTICAL COMPOSITIONS CONTAINING THEM

RELATED APPLICATIONS

Benefit under 35 U.S.C. § 119(e) of prior U.S. provisional application Ser. No. 60/249,350, filed Nov. 16, 2000, is hereby claimed.

BACKGROUND OF THE INVENTION

The present invention relates to new anticholinergics of general formula 1

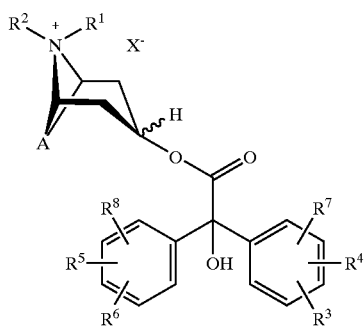

wherein A, X⁻, and the groups $R^1$, $R^2$, $R^3$, $R^4$, $R^5$, $R^6$, $R^7$, and $R^8$ have the meanings given herein, processes for preparing them, and their use as pharmaceutical compositions.

Anticholinergics may be used therapeutically in a variety of complaints. Particular mention should be made here, for example, of the treatment of asthma or chronic obstructive pulmonary disease (COPD). For treating these diseases WO 92/16528 proposes anticholinergics which have a scopine, tropenol, or tropine basic structure. The objective on which WO 92/16528 is based is to prepare compounds with an anticholinergic activity which are characterized by a long-lasting activity. To solve this problem, WO 92/16528 discloses, inter alia, benzilic acid esters of scopine, tropenol, or tropine.

For treating chronic diseases it is often desirable to prepare pharmaceutical compositions having a fairly long duration of activity. As a rule, this ensures that the concentration of the active substance needed in the body to achieve the therapeutic effect is provided over a fairly long period of time without having to administer the drug too frequently. Moreover, administering an active substance at fairly long time intervals makes a major contribution to the patient's well being. It is particularly desirable to provide a drug which can be used in a therapeutically beneficial manner by a single application per day (single dose). The use of a drug once a day has the advantage that the patient can become accustomed relatively quickly to regularly taking the drug at certain times of the day.

In order to be used as a medicament for use once a day, the active substance to be given must meet particular requirements. First of all, the onset of the desired activity should take place relatively quickly after administration of the drug and ideally should have as constant an effect as possible over a subsequent fairly long period of time. On the other hand, the duration of activity of the drug should not substantially exceed a period of about one day. Ideally, an active substance has an activity profile such that the preparation of a drug for administration once a day, which contains the active substance in therapeutically beneficial doses, can be deliberately controlled.

It has been found that the benzilic acid esters of scopine, tropenol, and tropine disclosed in WO 92/16528 do not meet these stringent requirements. Because of their extremely long period of activity, which significantly exceeds the above-mentioned period of about one day, they cannot be used therapeutically for administration in a single dose per day.

The aim of the present invention is therefore to provide new anticholinergics which, by virtue of their activity profile, make it possible to prepare a drug for administration once a day. A further objective of the invention is to prepare compounds characterized by a relative rapid onset of activity. The invention further sets out to provide compounds which, after a rapid onset of activity, have as constant an activity as possible over a subsequent lengthy period of time. A further aim of the invention is to provide compounds whose duration of activity does not substantially exceed a period of about one day in therapeutically beneficial doses. Finally, the invention sets out to provide compounds which have an activity profile which ensures good control of the therapeutic effect (i.e., total therapeutic effect without side effects caused by a build-up of the substance in the body).

DETAILED DESCRIPTION OF THE INVENTION

Surprisingly, it has been found that the above objectives are achieved by means of compounds of general formula 1 wherein at least one of the groups $R^3$, $R^4$, $R^5$, $R^6$, $R^7$, and $R^8$ does not represent hydrogen.

Accordingly, the present invention relates to compounds of general formula 1

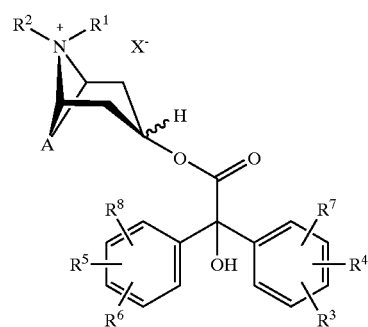

wherein:

A denotes a double-bonded group selected from among

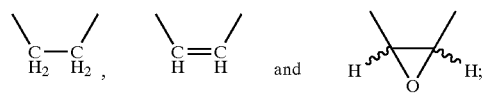

X⁻ denotes an anion with a single negative charge;

$R^1$ and $R^2$ denote $C_1$–$C_4$-alkyl which is optionally substituted by hydroxy or halogen; and $R^3$, $R^4$, $R^5$, $R^6$, $R^7$, and $R^8$, which may be identical or different, denote hydrogen, $C_1$–$C_4$-alkyl, $C_1$–$C_4$-alkyloxy, hydroxy, $CF_3$, CN, $NO_2$, or halogen, with the proviso that at least one of the groups $R^3$, $R^4$, $R^5$, $R^6$, $R^7$, and $R^8$ is not hydrogen.

Preferred compounds of general formula 1 are those wherein A denotes a double bonded group selected from among

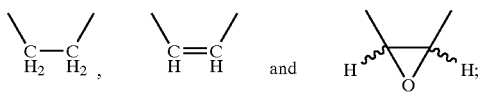

X⁻ denotes an anion with a single negative charge selected from among chloride, bromide, methylsulfate, 4-toluenesulfonate, and methanesulfonate, preferably bromide;

$R^1$ and $R^2$, which may be identical or different, denote a group selected from among methyl, ethyl, n-propyl, and isopropyl, which is optionally substituted by hydroxy or fluorine, preferably unsubstituted methyl; and $R^3$, $R^4$, $R^5$, $R^6$, $R^7$, and RS, which may be identical or different, denote hydrogen, methyl, ethyl, methyloxy, ethyloxy, hydroxy, fluorine, chlorine, bromine, CN, $CF_3$, or $NO_2$, with the proviso that at least one of the groups $R^3$, $R^4$, $R^5$, $R^6$, $R^7$, and $R^8$ is not hydrogen.

Particularly preferred are compounds of general formula 1, wherein A denotes a double-bonded group selected from among

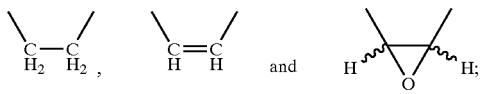

X⁻ denotes bromide;

$R^1$ and $R^2$, which may be identical or different, denote methyl or ethyl, preferably methyl; and $R^3$, $R^4$, $R^5$, $R^6$, $R^7$, and $R^8$, which may be identical or different, denote hydrogen, methyl, methyloxy, fluorine, chlorine, or bromine, with the proviso that at least one of the groups $R^3$, $R^4$, $R^5$, $R^6$, $R^7$, and $R^8$ is not hydrogen.

Of particular importance according to the invention are compounds of general formula 1, wherein A denotes a double-bonded group selected from among

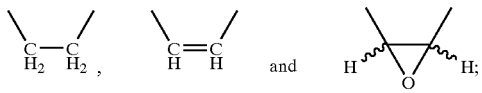

X⁻ denotes bromide;

$R^1$ and $R^2$, which may be identical or different, denote methyl or ethyl, preferably methyl; and $R^3$, $R^4$, $R^5$, $R^6$, $R^7$, and $R^8$, which may be identical or different, denote hydrogen, fluorine, chlorine, or bromine, with the proviso that at least one of the groups $R^3$, $R^4$, $R^5$, $R^6$, $R^7$, and $R^8$ is not hydrogen.

Also of particular importance according to the invention are compounds of general formula 1, wherein A denotes a double-bonded group selected from among

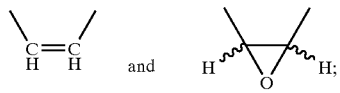

X⁻ denotes bromide;

$R^1$ and $R^2$ which may be identical or different denote methyl or ethyl, preferably methyl; and $R^3$, $R^4$, $R^5$, $R^6$, $R^7$, and $R^8$, which may be identical or different, denote hydrogen, fluorine, chlorine, or bromine, with the proviso that at least one of the groups $R^3$, $R^4$, $R^5$, $R^6$, $R^7$, and $R^8$ is not hydrogen.

Of outstanding importance according to the invention are the compounds of general formula 1, wherein A denotes a double-bonded group selected from among

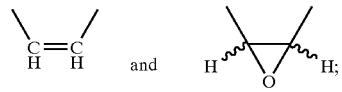

denotes bromide; $R^1$ and $R^2$ denote methyl; and $R^3$, $R^4$, $R^5$, $R^6$, $R^7$, and $R^8$, which may be identical or different, denote hydrogen or fluorine, with the proviso that at least one of the groups $R^3$, $R^4$, $R^5$, $R^6$, $R^7$, and $R^8$ is not hydrogen.

The invention relates to the compounds of formula 1, optionally in the form of the individual optical isomers, mixtures of the individual enantiomers, or racemates thereof.

In the compounds of general formula 1 the group $R^3$, $R^4$, $R^5$, $R^6$, $R^7$, and $R^8$, provided that they do not denote hydrogen, may each be in the ortho-, meta-, or para-position relative to the bond to the "—C—OH"-group. Provided that none of the groups $R^3$, $R^4$, $R^5$, $R^6$, $R^7$, and $R^8$ denotes hydrogen, $R^3$ and $R^5$ are preferably linked in the para-position and $R^4$, $R^6$, $R^7$, and $R^8$ are preferably linked in the ortho- or meta-position, most preferably in the meta-position. Particularly preferred are compounds of formula 1 wherein the groups $R^7$ and $R^8$ denote hydrogen. If in this case one of the groups $R^3$ and $R^4$ and one of the groups $R^5$ and $R^6$ denotes hydrogen, the other group in each case is preferably linked in the meta- or para-position, most preferably in the para-position. If none of the groups $R^3$, $R^4$, $R^5$, $R^6$, $R^7$, and $R^8$ denotes hydrogen, according to the invention the compounds of general formula 1 wherein the groups $R^3$, $R^4$, $R^5$, $R^6$, $R^7$, and $R^8$ have the same meaning are particularly preferred.

Of particular importance according to the invention are the compounds of general formula 1 wherein the ester-substituent on the nitrogen-bicyclic group is in the α-configuration. These compounds correspond to general formula 1-α

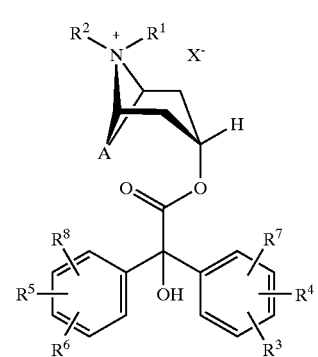

The following compounds are of particular significance according to the invention:
(a) tropenol 3,3',4,4'-tetrafluorobenzilate methobromide;
(b) scopine 3,3',4,4'-tetrafluorobenzilate methobromide;
(c) scopine 4,4'-dichlorobenzilate methobromide;
(d) scopine 4,4'-difluorobenzilate methobromide;
(e) tropenol 3,3'-difluorobenzilate methobromide;
(f) scopine 3,3'-difluorobenzilate methobromide; and
(g) tropenol 4,4'-difluorobenzilate ethyl bromide.

Unless otherwise stated, the alkyl groups are straight-chained or branched alkyl groups having 1 to 4 carbon atoms. The following are mentioned by way of example:

methyl, ethyl, propyl, or butyl. In some cases the abbreviations Me, Et, Prop, or Bu are used to denote the groups methyl, ethyl, propyl, or butyl. Unless otherwise stated, the definitions propyl and butyl include all the possible isomeric forms of the groups in question. Thus, for example, propyl includes n-propyl and isopropyl, butyl includes isobutyl, sec-butyl, and tert-butyl, etc.

Unless otherwise stated, the term alkyloxy groups denotes branched and unbranched alkyl groups having 1 to 4 carbon atoms which are linked via an oxygen atom. Examples of these include: methyloxy, ethyloxy, propyloxy, or butyloxy. The abbreviations MeO-, EtO-, PropO-, or BuO- are used in some cases to denote the groups methyloxy, ethyloxy, propyloxy, or butyloxy. Unless otherwise stated, the definitions propyloxy and butyloxy include all possible isomeric forms of the groups in question. Thus, for example, propyloxy includes n-propyloxy and isopropyloxy, butyloxy includes isobutyloxy, sec-butyloxy, and tert-butyloxy, etc. In some cases, within the scope of the present invention, the term alkoxy is used instead of the term alkyloxy. Accordingly, the terms methoxy, ethoxy, propoxy, or butoxy may also be used to denote the groups methyloxy, ethyloxy, propyloxy, or butyloxy.

Halogen within the scope of the present invention denotes fluorine, chlorine, bromine, or iodine. Unless stated otherwise, bromine is the preferred halogen.

The compounds according to the invention may partly be prepared, as illustrated below, analogously to procedures which are already known from the prior art (Diagram 1).

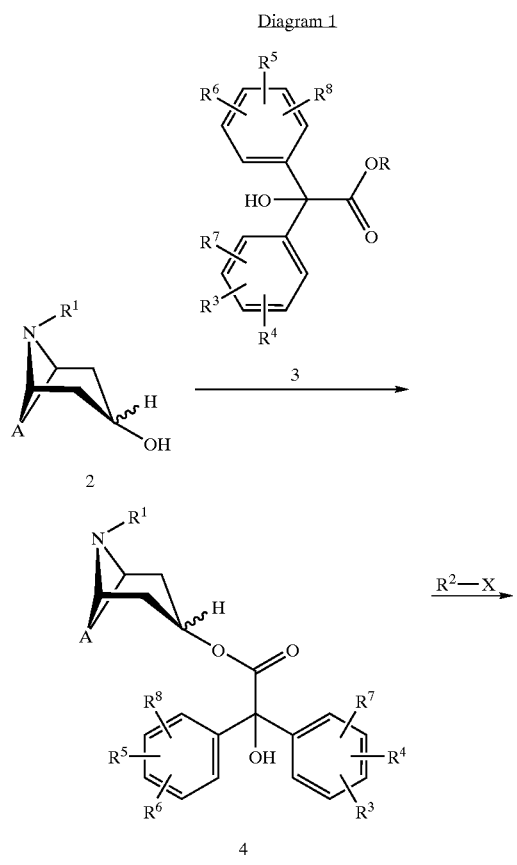

Diagram 1

Starting from the compounds of formula 2, the esters of general formula 4 may be obtained by reacting with the benzilic acid esters of formula 1, wherein R denotes a $C_1$–$C_4$-alkyl group, for example. This reaction may be carried out, for example, in a sodium melt at elevated temperature, preferably at about 50° C.–150° C., particularly preferably at about 90° C.–100° C. at low pressure, preferably below 500 mbar, most preferably below 75 mbar. Alternatively, instead of the benzilic acid esters 3, the corresponding α-chlorine compounds may be used (Cl instead of OH). In this case the reaction may be carried out analogously to the examples of synthesis disclosed in WO 92/16528, to which reference is hereby made in its entirety. The compounds of formula 4 thus obtained can be converted into the target compounds of formula 1 by reacting with the compounds $R^2$—X wherein $R^2$ and X may be as hereinbefore defined. This synthesis step may also be carried out analogously to the examples of synthesis disclosed in WO 92/16528.

Alternatively to the method of synthesizing the compounds of formula 4 illustrated in Diagram 1, the derivatives 4 wherein the nitrogen bicyclic group denotes a scopine-derivative may be obtained by oxidizing compounds of formula 4 wherein the bicyclic nitrogen group is a tropenyl group. This may be done as follows, according to the invention.

The compound 4 wherein A denotes —CH═CH—, is suspended in a polar organic solvent, preferably in a solvent selected from among N-methyl-2-pyrrolidone (NP), dimethylacetamide, and dimethylformamide, preferably dimethylformamide, and then heated to a temperature of about 30° C.–90° C., preferably 40° C.–70° C. Then a suitable oxidizing agent is added and the mixture is stirred at constant temperature for 2 to 8 hours, preferably 3 to 6 hours. The preferred oxidizing agent is vanadium pentoxide mixed with $H_2O_2$, most preferably $H_2O_2$-urea complex combined with vanadium pentoxide. The mixture is worked up in the usual way. The products may be purified by crystallization or chromatography, depending on their crystallization tendencies.

As shown in Diagram 1, the intermediate products of general formula 4 are of crucial importance. Accordingly, in another aspect, the present invention relates to the intermediates of formula 4

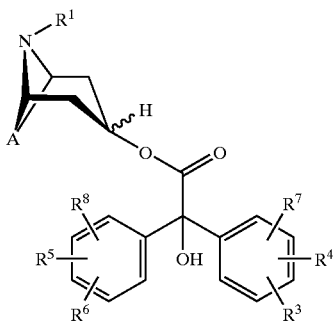

wherein;

A denotes a double-bonded group selected from among

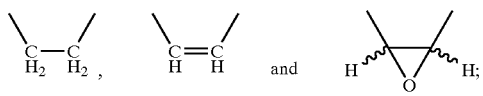

$R^1$ denotes $C_1$–$C_4$-alkyl which is optionally substituted by hydroxy or halogen; and $R^3$, $R^4$, $R^1$, $R^6$, $R^7$, and $R^8$, which may be identical or different, denote hydrogen, $C_1$–$C_4$-alkyl, $C_1$–$C_4$-alkyloxy, hydroxy, $CF_3$, CN, $NO_2$, or halogen, with the proviso that at least one of the groups $R^3$, $R^4$, $R^5$, $R^6$, $R^7$, and $R^8$ is not hydrogen.

The intermediates of general formula 4 are preferred wherein A denotes a double-bonded group selected from among

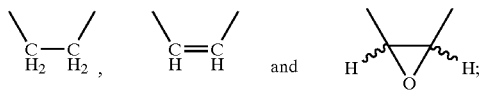

$R^1$ methyl, ethyl, n-propyl, and isopropyl, which is optionally substituted by hydroxy or fluorine, preferably unsubstituted methyl; and $R^3$, $R^4$, $R^5$, $R^6$, $R^7$, and $R^8$, which may be identical or different, denote hydrogen, methyl, ethyl, methyloxy, ethyloxy, hydroxy, fluorine, chlorine, bromine, CN, $CF_3$, or $NO_2$, with the proviso that at least one of the groups $R^3$, $R^4$, $R^5$, $R^6$, $R^7$, and $R^8$ is not hydrogen.

Particularly preferred are the intermediates of general formula 4, wherein A denotes a double-bonded group selected from among

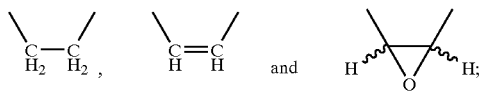

$R^1$ denotes methyl or ethyl, preferably methyl; and
$R^3$, $R^4$, $R^5$, $R^6$, $R^7$, and $R^8$, which may be identical or different, denote hydrogen, methyl, methyloxy, fluorine, chlorine, or bromine, with the proviso that at least one of the groups $R^3$, $R^4$, $R^5$, $R^6$, $R^7$, and $R^8$ is not hydrogen.

Of particular importance according to the invention are the intermediates of general formula 4, wherein A denotes a double-bonded group selected from among

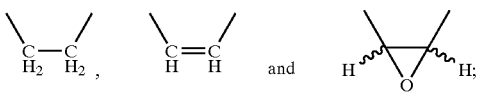

$R^1$ denotes methyl or ethyl, preferably methyl; and
$R^3$, $R^4$, $R^5$, $R^6$, $R^7$, and $R^8$, which may be identical or different, denote hydrogen, fluorine, chlorine, or bromine, with the proviso that at least one of the groups $R^3$, $R^4$, $R^5$, $R^6$, $R^7$, and $R^8$ is not hydrogen.

Also of particular importance according to the invention are the intermediates of formula 4, wherein A denotes a double-bonded group selected from among

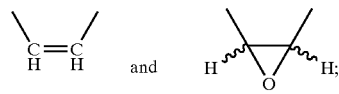

$R^1$ denotes methyl or ethyl, preferably methyl; and
$R^3$, $R^4$, $R^5$, $R^6$, $R^7$, and $R^8$, which may be identical or different, denote hydrogen, fluorine, chlorine, or bromine, with the proviso that at least one of the groups $R^3$, $R^4$, $R^5$, $R^6$, $R^7$, and $R^8$ is not hydrogen.

Of exceptional importance according to the invention are the intermediates of general formula 4, wherein A denotes a double-bonded group selected from among

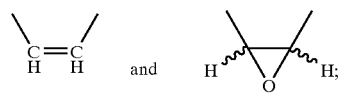

$R^1$ denotes methyl; and
$R^3$, $R^4$, $R^5$, $R^6$, $R^7$, and $R^8$, which may be identical or different, denote hydrogen or fluorine, with the proviso that at least one of the groups $R^3$, $R^4$, $R^5$, $R^6$, $R^7$, and $R^8$ is not hydrogen.

As in the compounds of general formula 1, in the intermediates of formula 4 the groups $R^3$, $R^4$, $R^5$, $R^6$, $R^7$, and $R^8$, if they do not represent hydrogen, may be in the ortho-, meta-, or para-position relative to the bond to the "—C—OH" group. If none of the groups $R^3$, $R^4$, $R^5$, $R^6$, $R^7$, and $R^8$ denotes hydrogen, $R^3$ and $R^5$ are preferably linked in the para-position and $R^4$, $R^6$, $R^7$, and $R^8$ are preferably linked in the ortho- or meta-position, most preferably in the meta-position. Particularly preferred are intermediates of formula 4 wherein $R^7$ and $R^8$ denote hydrogen. If in this case one of the groups $R^3$ and $R^4$ and one of the groups $R^5$ and $R^6$ denote hydrogen, the other group in each case is preferably linked in the meta- or para-position, most preferably in the para-position. If none of the groups $R^3$, $R^4$, $R^5$, $R^6$, $R^7$, and $R^8$ denotes hydrogen, according to the invention the intermediates of general formula 4 wherein the groups $R^3$, $R^4$, $R^5$, $R^6$, $R^7$, and $R^8$ have the same meaning are particularly preferred.

In order to prepare the intermediate products of general formula 4, correspondingly substituted benzilic acid derivatives of general formula 3 are used. These are obtained, analogously to methods known in the art, by reacting Grignard reagents generated in situ from the bromides 5 with the aromatic α-carbonyl-carboxylic acid esters 6.

Diagram 2

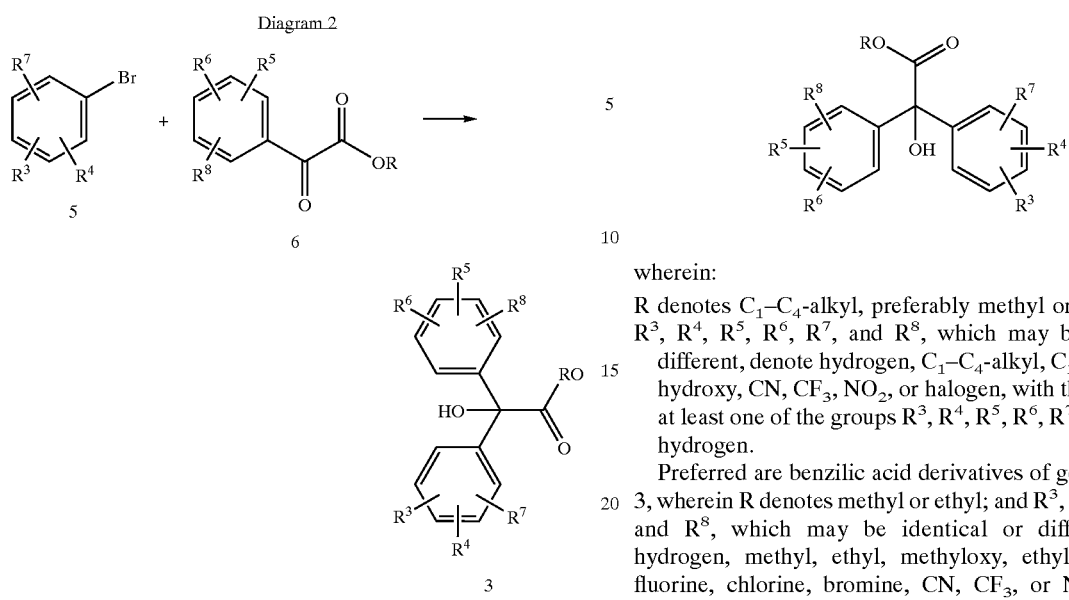

Diagram 2

The reaction is carried out in anhydrous organic solvents, preferably in ethereal solvents, most preferably in a solvent selected from among diethylether, dioxane, and tetrahydrofuran (THF), the latter being particularly significant. The Grignard reagent is generated from the bromides 5 by reacting with Mg chips. In some cases it may be necessary to add a reaction starter such as iodine or dibromoethane. In order to complete the formation of Grignard-reagent it may be necessary to heat the reaction mixture over a period of 0.5 to 2 hours, preferably to above 30° C., most preferably to above 50° C. The upper limit of the temperature range which may be used will naturally be determined from the boiling temperature of the solvent used. The Grignard-reagent thus obtained is then slowly added dropwise to a solution of 6 in one of the above-mentioned solvents. The work may be done at ambient temperature, but is preferably done at a temperature in the range from 0° C.–15° C. The reaction is generally complete after 1 to 4 hours. The mixture is worked up by conventional methods. The products are purified by crystallization or column chromatography, depending on the crystallization tendencies of the compounds S.

Alternatively, the compounds of formula 3 may also be obtained analogously to other methods of synthesis known from the prior art. Where, for example, suitably substituted benzilic acids are already known in the art and are commercially available, the compounds of formula 3 may also be obtained directly from them by acid- or base-catalyzed esterification with the corresponding alcohols R—OH. Where suitably substituted benzils are already known from the art and are commercially available, the compounds of formula 3 may also be obtained directly from them by benzilic acid rearrangement and subsequent acid- or base-catalyzed esterification with the corresponding alcohols R—OH.

As can be seen from Diagram 1, the benzilic acid derivatives of general formula 3 have a central importance in preparing the compounds of general formula 4 and thus those of formula 1 as well.

Accordingly, in another aspect, the present invention relates to benzilic acid derivatives of general formula 3 wherein:

R denotes $C_1$–$C_4$-alkyl, preferably methyl or ethyl; and $R^3$, $R^4$, $R^5$, $R^6$, $R^7$, and $R^8$, which may be identical or different, denote hydrogen, $C_1$–$C_4$-alkyl, $C_1$–$C_4$-alkyloxy, hydroxy, CN, $CF_3$, $NO_2$, or halogen, with the proviso that at least one of the groups $R^3$, $R^4$, $R^5$, $R^6$, $R^7$, and $R^8$ is not hydrogen.

Preferred are benzilic acid derivatives of general formula 3, wherein R denotes methyl or ethyl; and $R^3$, $R^4$, $R^5$, $R^6$, $R^7$, and $R^8$, which may be identical or different, denote hydrogen, methyl, ethyl, methyloxy, ethyloxy, hydroxy, fluorine, chlorine, bromine, CN, $CF_3$, or $NO_2$, with the proviso that at least one of the groups $R^3$, $R^4$, $R^5$, $R^6$, $R^7$, and $R^8$ is not hydrogen.

Particularly preferred are benzilic acid derivatives of general formula 3, wherein R denotes methyl or ethyl; and $R^3$, $R^4$, $R^5$, $R^6$, $R^7$, and $R^8$, which may be identical or different, denote hydrogen, methyl, methyloxy, fluorine, chlorine, or bromine, with the proviso that at least one of the groups $R^3$, $R^4$, W, $R^6$, $R^7$, and $R^8$ is not hydrogen.

Of particular importance according to the invention are benzilic acid derivatives of general formula 3, wherein R denotes methyl or ethyl; and $R^3$, $R^4$, $R^5$, $R^6$, $R^7$, and $R^8$, which may be identical or different, denote hydrogen, fluorine, chlorine, or bromine, with the proviso that at least one of the groups $R^3$, $R^4$, $R^5$, $R^6$, $R^7$, and $R^8$ is not hydrogen.

Of exceptional importance according to the invention are the intermediates of general formula 3, wherein R denotes methyl or ethyl; and $R^3$, $R^4$, $R^5$, $R^6$, $R^7$, and $R^8$, which may be identical or different, denote hydrogen or fluorine, with the proviso that at least one of the $R^3$, $R^4$, $R^5$, $R^6$, $R^7$, and $R^8$ is not hydrogen.

As in the compounds of general formula 4 and 1, in the benzilic acid derivatives of formula 3 the groups $R^3$, $R^4$, $R^5$, $R^6$, $R^7$, and $R^8$, provided that they are not hydrogen, may each be in the ortho-, meta-, or para-position relative to the bond to the "—C—OH" group. If none of the groups $R^3$, $R^4$, $R^5$, $R^6$, $R^7$, and $R^8$ denotes hydrogen, $R^3$ and $R^5$ are preferably linked in the para-position and $R^4$, $R^5$, $R^6$, $R^7$, and $R^8$ are preferably linked in the ortho- or meta-position, most preferably in the meta-position. Particularly preferred are benzilic acids of formula 3 wherein $R^7$ and $R^8$ denote hydrogen. If one of the groups $R^3$ and $R^4$ and one of the groups $R^5$ and $R^6$ denotes hydrogen, the other group in each case is preferably linked in the meta- or para-position, most preferably in the para-position. If none of the groups $R^3$, $R^4$, $R^5$, $R^6$, $R^7$, and $R^8$ denotes hydrogen, according to the invention the benzilic acid derivatives of general formula 3 wherein the groups $R^3$, $R^4$, $R^5$, $R^6$, $R^7$, and $R^1$ have the same meaning are particularly preferred.

The examples of synthesis described hereinafter serve to illustrate the present invention still further. However, they are intended only as examples of procedures as an illustration of the invention without restricting the invention to the subject-matter described by way of example.

I. Synthesis of the Benzilic Acid Derivatives of General Formula 3

I.1: ethyl 3,3',4,'-tetrafluorobenzilate 3a

The Grignard reagent is prepared from 2.24 g (0.092 mol) of magnesium chips, a few granules of iodine, and 17.80 g (0.092 mol) of 1-bromo-3,4-difluorobenzene in 100 ml of THF at 50° C. After the halide has all been added, the mixture is stirred for another hour. The Grignard reagent thus obtained is added dropwise to 18.81 g (0.088 mol) of ethyl 3,4-difluorophenylglyoxylate in 80 ml of THF at 10° C.–15° C. and the mixture obtained is stirred for 2 hours at 5° C. The white suspension is poured onto ice/sulfuric acid for working up, extracted with ethyl acetate, the organic phase is washed with water, dried over $MgSO_4$ and evaporated to dryness. The crude product is purified by column chromatography (eluant: toluene). Yield: 10.80 g (38% of theory).

I.2: methyl 2,2'-dichlorobenzilate 3b

A solution of 10.0 g (0.034 mol) of 2,2'-dichlorobenzilic acid in 50 ml of ethanol was added dropwise to freshly prepared sodium ethoxide solution of 0.78 g (0.034 mol) of sodium and 100 ml of ethanol at 20° C. and stirred overnight. The solution was evaporated to dryness, the residue was dissolved in DMF and at 20° C. 9.57 g (0.0674 mol) of methyl iodide were added dropwise and the mixture was stirred for a further 72 hours. 300 ml of water were added dropwise to the resulting suspension while cooling with ice, it was extracted with diethyl ether, the organic phase was washed with water, dried over $Na_2SO_4$, and evaporated to dryness. Yield: 10.48 g (100% of theory).

I.3: methyl 4,4'-difluorobenzilate 3c

I.3.1: 4,4'-difluorobenzilic acid

At about 100° C., a solution of 24.62 g (0.1 mol) of 4,4'-difluorobenzil in 250 ml of dioxane is added dropwise to a solution of 49.99 g (1.25 mol) of NaOH flakes in 300 ml of water and stirred for 2 hours. The dioxane is largely distilled off and the aqueous solution remaining is extracted with dichloromethane. When the aqueous solution is acidified with sulfuric acid, a precipitate is formed which is suction filtered, washed, and dried. The filtrate is extracted with dichloromethane, the organic phase is dried over $Na_2SO_4$ and evaporated to dryness. Yield: 25.01 g (95% of theory); melting point: 133° C.–136° C.

I.3.2: methyl 4,4'-difluorobenzilate 25.0 g (0.095 mol) of 4,4'-difluorobenzilic acid is added to freshly prepared sodium ethoxide solution containing 2.17 g (0.095 mol) of sodium and 200 ml of ethanol at 20° C. and stirred for 3 hours. The solution is evaporated to dryness, the residue is dissolved in DMF, 22.57 g (0.16 mol) of methyl iodide is added dropwise at 20° C., and the mixture is stirred for 24 hours. It is worked up and purified analogously to compound 12b. Yield: 21.06 g (80% of theory).

I.4: methyl 2,2',4,4'-tetrafluorobenzilate 3d

I.4.1: methyl 2,4-difluorophenylglyoxylate 50 g (0.44 mol) of 1,3-difluorobenzene is dissolved at 20° C. in 135 ml of carbon disulfide with 73.5 g (0.55 mol) $AlCl_3$ and then 55.15 g (0.45 mol) of methyl oxalate chloride is added and the mixture is stirred for 2.5 hours at 20° C. Ice-cold 2 N aqueous hydrochloric acid is added dropwise while cooling, extracted with ethyl acetate; the organic phase is washed with water and 10% aqueous $Na_2CO_3$ solution, dried over $MgSO_4$, and evaporated to dryness. Yield: 38.0 g (43% of theory).

I.4.2: methyl 2,2',4,4'-tetrafluorobenzilate

Starting from the methyl 2,4-difluorophenylglyoxylate obtained according to the above procedure, the title compound is prepared analogously to 3a. Yield: 7.55 g (13% of theory).

I.5: methyl 4,4'-dimethylbenzilate 3e

At 20° C., 12.43 g (0.048 mol) of 4,4'-methylbenzilic acid in 50 ml of ethanol is added dropwise to freshly prepared sodium ethoxide solution containing 1.1 g (0.045 mol) of sodium and 100 ml of ethanol and the mixture is stirred for 30 minutes. The solution is evaporated to dryness, the residue dissolved in 50 ml of DMF, 9.08 g (0.064 mol) of methyl iodide is added dropwise at 20° C., and stirring is continued for a further 24 hours. 300 ml of water are added dropwise to the resulting suspension while cooling with ice, the mixture is extracted with diethylether, the organic phase is washed with water, dried over $Na_2SO_4$, and evaporated to dryness. Yield: 8.6 g (99% of theory); melting point: 83° C.–84° C.

I.6: methyl 3,3',4,4'-tetramethoxybenzilate 3f

I.6.1: methyl 3,4-dimethoxyglyoxylate 14.00 g (0.11 mol) of $AlCl_3$ are placed in 100 ml of dichloromethane and at 5° C. combined with 12.86 g (0.11 mol) of monomethyl oxalate chloride. 1,2-dimethoxybenzene is added dropwise to the organic solution at 0° C., the mixture is stirred for 1 hours at 0° C., then for 24 hours at 20° C., poured onto ice/hydrochloric acid, and extracted; the organic phase is washed with water and $NaHCO_3$ solution, dried over $MgSO_4$, and evaporated to dryness. The residue is crystallized from diethylether/petroleum ether. Yield: 13.55 g (60% of theory); melting point: 65° C.–66° C.

I.6.2: methyl 3,3',4,4'-tetramethoxybenzilate

The Grignard reagent is prepared from 1.58 g (0.065 mol) of magnesium chips, some iodine, and 14.10 g (0.065 mol) of bromoveratrole in 50 ml of THF at 50° C. Stirring is continued for 1 hour. 11.28 g (0.05 mol) of methyl 3,4-dimethoxyglyoxylate are placed in 80 ml of THF and the Grignard reagent is added dropwise at 10° C.–15° C., the mixture is stirred for 2 hours at 20° C., poured onto ice/sulfuric acid, and extracted with ethyl acetate. Then the organic phase is washed with water, dried over $MgSO_4$, and evaporated to dryness. The product is purified by crystallization from acetone/diethylether. Yield: 7.62 g (42% of theory); melting point: 129° C.–130° C.

I.7: methyl 4,4'-dimethoxybenzilate 3g

I.7.1: methyl 4-methoxyglyoxylate

The compound is prepared analogously to step I.6.1 starting from 21.65 g (0.20 mol) of anisole; Yield: 16.45 g (60% of theory); melting point: 52° C.

I.7.2: methyl 3,4-dimethoxybenzilate

The compound is prepared analogously to step I.6.2, starting from 16.45 g (0.085 mol) of methyl 4-methoxyglyoxylate; the product is purified by crystallization from isopropanol; Yield: 12.28 g (48% of theory); melting point: 111° C.

I.8: methyl 3,3'-dimethyl-4,4'-dimethoxybenzilate 3h

I.8.1: methyl 3-methyl-4-methoxyglyoxylate:

The compound is prepared analogously to step I.6.1 starting from 26.88 g (0.22 mol) of 2-methylanisol. Yield: 21.0 g (46% of theory); melting point: 49° C.

I.8.2: methyl 3,4-dimethoxybenzilate

The compound is prepared analogously to step I.6.2, starting from 21.0 g (0.1 mol) of methyl 3-methyl-4-methoxyglyoxylate; the product is purified by crystallization from petroleum ether/diethylether. Yield: 11.1 g (33% of theory); melting point: 134° C.

I.9 ethyl 4,4'-dichlorobenzilate 3i

The product may be synthesized analogously to step I.5.

I.10: methyl 3,3',5,5'-tetrafluorobenzilate 3j

I.10.1: 3,3',5,5'-tetrafluorobenzil 110 ml of ethanol are taken at ambient temperature and 50.0 g (0.352 mol) of 3,5-difluorobenzaldehyde and 444 g (0.018 mol) of 3-ethyl-5-(2-hydroxyethyl)-4-methylthiazolium bromide is added. Then 10.7 g (0.11 mol) of triethylamine is added dropwise. The mixture is refluxed for 3 hours and evaporated to dryness. The residue is taken up in ethyl acetate and extracted with water, sodium pyrosulfite in water, and $Na_2CO_3$ solution. After drying over $MgSO_4$, the mixture is evaporated to dryness. Yield: 39.91 g of yellow crystals (80% of theory).

39.91 g of the acyloin thus obtained is dissolved in 1700 ml of acetonitrile at ambient temperature, 0.2 ml of vanadium-(V)-oxytrichloride is added, and oxygen is piped in. After 1.5 hours, the solution is evaporated to dryness, extracted with ethyl acetate and water, as well as $Na_2CO_3$ solution, dried over $MgSO_4$, and evaporated to dryness. The residue remaining is stirred with petroleum ether/ethyl acetate 95:5. Yield: 26.61 g yellowish-green crystals (67% of theory); melting point: 136° C.–138° C.

I.10.2: 3,3',5,5'-Tetrafluorobenzilic acid 46.98 g (1.747 mol) of sodium hydroxide in 330 ml water are placed in a boiling water bath with thorough stirring and a solution of 26.61 g (0.094 mol) of 3,3',5,5'-tetrafluorobenzil in 330 ml dioxane is added dropwise and then stirred for another 1 hour. After cooling, the dioxane is evaporated; the residue is diluted with water and extracted with diethylether. The organic phase is acidified, extracted with dichloromethane, dried over $MgSO_4$, evaporated to dryness. Yield: 20.15 g of yellowish crystals (71% of theory).

I.10.3: methyl 3,3',5,5'-tetrafluorobenzilate 20.15 g (0.0671 mol) of 3,3',5,5'-tetrafluorobenzilic acid are placed in 250 ml acetonitrile, 18.6 g (0.121 mol) of DBU, and 34.4 g (0.2426 mol) of methyl iodide is added and then stirred for 6 hours at ambient temperature. The reaction mixture is evaporated to dryness, the residue extracted with ethyl acetate and water, the organic phase dried over $MgSO_4$, evaporated to dryness. The product is recrystallized from cyclohexane. Yield: 15.11 g of beige crystals (68% of theory); melting point: 113° C.–114° C.

I.11: methyl 3,3'-dichlorobenzilate 3k

I.11.1: 3,3'-dichlorobenzil 100 ml of ethanol are used at ambient temperature and 50.0 g (0.356 mol) of 3-chlorobenzaldehyde and 4.54 g (0.018 mol) of 3-ethyl-5-(2-hydroxyethyl)-4-methylthiazolium bromide are added. Then 10.7 g (0.11 mol) of triethylamine is added dropwise. The mixture is refluxed for 3 hours and evaporated to dryness. The residue is taken up in ethyl acetate and extracted with water, sodium pyrosulfite in water, and $Na_2CO_3$ solution. After drying over $MgSO_4$, it is evaporated to dryness. The product obtained is recrystallized from isopropanol and petroleum ether. Yield: 13.2 g of white crystals (13% of theory); melting point 69° C.–70° C.

13.0 g of the acyloin thus obtained is dissolved in 460 ml acetonitrile at RT, 0.0867 g of vanadium-(V)-oxytrichloride is added and oxygen is piped in. After 1.5 hours, the solution is evaporated to dryness, extracted with ethyl acetate and water, as well as $Na_2CO_3$ solution, dried over $MgSO_4$, and evaporated to dryness. The residue remaining is stirred with petroleum ether/ethyl acetate 95:5. Yield: 12.59 g of yellow crystals (97% of theory); melting point: 116° C.–117° C.

I.11.2: 3,3'-dichlorobenzilic acid 51.45 g (1.286 mol) of sodium hydroxide in 1000 ml water are placed in a bath of boiling water with thorough stirring and a solution of 28.5 g (0.102 mol) of 3,3'-dichlorobenzil in 700 ml dioxane is added dropwise and then stirred for another 1 hour. After cooling, the dioxane is evaporated down, the residue is diluted with water and extracted with diethylether. The organic phase is acidified, extracted with dichloromethane, dried over $MgSO_4$, evaporated to dryness. Yield: 32.7 g (71% of theory).

I.11.3: methyl 3,3'-dichlorobenzilate

From 100 ml of ethanol and 1.97 g (0.0855 mol) of sodium, a sodium ethoxide solution is prepared to which 26.6 g (0.0855 mol) of 3,3'-dichlorobenzilic acid in 50 ml of ethanol is added dropwise. The mixture is then stirred for 4 hours at ambient temperature. After the solvent has been distilled off, the residue is dissolved in 150 ml DMF and 24.27 g (0.171 mol) of methyl iodide is added dropwise, then stirred for another 24 hours. While cooling with ice, 300 ml of water and 200 ml of diethylether are added dropwise, the phases are separated, the aqueous phase is extracted with diethylether, then the organic phases are washed with $Na_2CO_3$ solution and shaken with water till neutral. After drying over $Na_2SO_4$, the mixture is evaporated to dryness. Yield: 22.91 g of yellow oil (82% of theory).

I.12: methyl 4,4'-di(trifluoromethyl)benzilate 3l

I.12.1: 4,4'-di(trifluoromethyl)benzil

The reaction to form the acyloin derivative is carried out analogously to the process according to step I.11.1 starting from 174.1 g of 4-(trifluoromethyl)benzaldehyde. Yield: 150.2 g of whitish-yellow crystals (86% of theory).

150.2 g of the acyloin thus obtained are reacted analogously to the method according to step I.11.1 to obtain the benzil. Yield: 93.5 g of yellow crystals (63% of theory); melting point: 141° C.–142° C.

I.12.2: 4,4'-di(trifluoromethyl)benzilic acid 10.00 g (0.0289 mol) of 4,4'-di(trifluoromethyl)benzil are reacted analogously to the method according to step I.11.2 to obtain the corresponding benzilic acid. Yield: 8.15 g of yellowish crystals (77% of theory).

I.12.3: methyl 4,4'-di(trifluoromethyl)benzilate 38.5 g (0.115 mol) of 4,4'-di(trifluoromethyl)benzilic acid, 30.5 g (0.20 mol) of DBU, and 56.8 g (0.40 mol) of methyl iodide are reacted in 400 ml acetonitrile analogously to step I.10.3. The product is purified by flash chromatography (eluant cyclohexane/ethyl acetate 95:5). Yield: 20.05 g of white crystals (46% of theory); melting point: 68° C.

I.13: methyl 3,3'-di(trifluoromethyl)benzilate 3m

I.13.11: 3,3'-di(trifluoromethyl)benzil

The reaction to form the acyloin derivative is carried out analogously to the process according to step I.11.1 starting from 30.0 g of 3-trifluoromethyl)benzaldehyde. Yield: 25.96 g of yellow oil (87% of theory).

25.96 g of the acyloin thus obtained are reacted analogously to the method according to step I.11.1 to obtain the benzil. Yield: 10.5 g of light yellow crystals (24% of theory).

I.13.2: 3,3'-di(trifluoromethyl)benzilic acid 10.5 g (0.0182 mol) of 3,3'-di(trifluoromethyl)benzil are reacted analogously to the method according to step I.11.2 to obtain the corresponding benzilic acid. Yield: 10.55 g of yellowish oil.

I.13.3: methyl 3,3'-di(trifluoromethyl)benzilate 10.55 g (0.0289 mol) of 4,4'-di(trifluoromethyl)benzilic acid, 8.82 g (0.0579 mol) of DBU, and 16.44 g (0.1158 mol) of methyl iodide are reacted in 110 ml acetonitrile analogously to step I.10.3. The product is purified by recrystallization from cyclohexane. Yield: 6.02 g of white crystals (57% of theory); melting point: 69° C.–70° C.

I.14: methyl 3,3'-dichloro-4,4'-difluorobenzilate 3n

I.14.1: 3,3'-dichloro-4,4'-difluorobenzil

The reaction to form the acyloin derivative is carried out analogously to the process according to step I.11.1 starting from 30.0 g of 3-chloro-4-fluorobenzaldehyde. Yield: 29.49 g of orange oil.

29.49 g of the acyloin thus obtained are reacted analogously to the method according to step I.11.1 to obtain the benzil. Yield: 24.88 g of yellow crystals.

I.14.2: 3,3'-dichloro-4,4'-difluorobenzilic acid 24.88 g (0.079 mol) of 3,3'-dichloro-4,4'-difluorobenzil are reacted analogously to the method according to step I.11.2 to obtain the corresponding benzilic acid. Yield: 17.07 g of orange solid.

I.14.3: methyl 3,3'-dichloro-4,4'-difluorobenzilate 17.07 g (0.0512 mol) of 3,3'-dichloro-4,4'-difluorobenzilic acid, 14.10 g (0.0926 mol) of DBU, and 26.29 g (0.1852 mol) of methyl iodide are reacted in 200 ml acetonitrile analogously to step I.10.3. Yield: 6.77 g (38% of theory).

I.15: methyl 2 2',5,5'-tetrafluorobenzilate 3o

I.15.1: 2,2',5,5'-tetrafluorobenzil

The reaction to form the acyloin derivative is carried out analogously to the process according to step I.11.1 starting from 50.0 g 2,5-difluorobenzaldehyde. Yield: 45.5 g of yellow crystals.

45.5 g of the acyloin thus obtained are reacted analogously to the method according to step I.11.1 to obtain the benzil. Yield: 39.75 g of yellow crystals (88% of theory).

I.15.2: 2,2',5,5'-tetrafluorobenzilic acid 39.75 g (0.14 mol) of 2,2',5,5'-tetrafluorobenzil are reacted analogously to the method according to step I.11.2 to obtain the corresponding benzilic acid. Yield: 44.76 g of yellowish oil.

I.15.3: methyl 2,2',5,5'-tetrafluorobenzilate 44.76 g (0.14 mol) of 2,2',5,5'-tetrafluorobenzilbenzilic acid are reacted analogously to step I.10.3. Yield: 29.4 g of oil.

I.16: methyl 2,2',3,3'-tetrafluorobenzilate 3p

I.16.1: 2,2',3,3'-tetrafluorobenzil

The reaction to form the acyloin derivative is carried out analogously to the process according to step I.11.1 starting from 30.0 g 2,3-difluorobenzaldehyde. Yield: 29.85 g of yellow crystals.

29.85 g of the acyloin thus obtained are reacted analogously to the method according to step I.11.1 to obtain the benzil. Yield: 25.22 g of orange oil.

I.16.2: 2,2',3,3'-tetafluorobenzilic acid 25.22 g (0.0894 mol) of 2,2',3,3'-tetrafluorobenzil are reacted analogously to the method according to step I.11.2 to obtain the corresponding benzilic acid. Yield: 29.13 g of orange solid.

I.16.3: methyl 2,2',3,3'-tetrafluorobenzilate 29.13 g (0.097 mol) of 2,2',3,3'-tetrafluorobenzilbenzilic acid are reacted analogously to step I.10.3. Yield: 15.78 g of beige crystals; melting point: 102° C.–103° C.

I.17: methyl 3,3'-difluorobenzilate 3q

I.17.1: 3,3'-difluorobenzil

The reaction to form the acyloin derivative is carried out analogously to the process according to step I.11.1 starting from 50.0 g 3-fluorobenzaldehyde. Yield: 49.45 g.

49.45 g of the acyloin thus obtained are reacted analogously to the method according to step I.11.1 to obtain the benzil. Yield: 42.01 g of light yellow crystals; melting point: 104° C.–105° C.

I.17.2: 3,3'-difluorobenzilic acid 42.01 g (0.171 mol) of 3,3'-difluorobenzil are reacted analogously to the method according to step I.11.2 to obtain the corresponding benzilic acid. Yield: 33.07 g (75% of theory); melting point: 121° C.–122° C.

I.17.3: methyl 3,3'-difluorobenzilate 33.7 g (0.128 mol) of 3,3'-difluorobenzilbenzilic acid are reacted analogously to step I.10.3. Yield: 34.78 g beige crystals (98% of theory); melting point: 84° C.–85° C.

I.18: methyl 4,4'-dichloro-3,3'-difluorobenzilate 3r

I.18.1: 4,4'-dichloro-3,3'-difluorobenzil

The reaction to form the acyloin derivative is carried out analogously to the process according to step I.11.1 starting from 33.13 g 4-chloro-3-fluorobenzaldehyde. Yield: 30.07 g of oil.

30.07 g of the acyloin thus obtained are reacted analogously to the method according to step I.11.1 to obtain the benzil. Yield: 19.32 g of light yellow powder.

I.18.2: 4,4'-dichloro-3,3'-difluorobenzilic acid 19.32 g (0.0613 mol) of 4,4'-dichloro-3,3'-difluorobenzil are reacted analogously to the method according to step I.11.2 to obtain the corresponding benzilic acid. Yield: 25.3 g of oil.

I.18.3: methyl 4,4'-dichloro-3,3'-difluorobenzilate 25.3 g (0.075 mol) of 4,4'-dichloro-3,3'-difluorobenzilic acid are reacted analogously to step I.10.3. Yield: 13.07 g of yellow oil (50% of theory).

I.19: methyl 3,3',4,4'-tetrachlorobenzilate 3s

I.19.1: 3,3',4,4'-tetrachlorobenzil

The reaction to form the acyloin derivative is carried out analogously to the process according to step I.11.1 starting from 100 g of 3,4-dichlorobenzaldehyde. Yield: 60.89 g of oil.

60.89 g of the acyloin thus obtained are reacted analogously to the method according to step I.11.1 to obtain the benzil. Yield: 42.45 g of yellow crystals.

I.19.2: 3,3',4,4'-tetrachlorobenzilic acid 44.75 g (0.128 mol) of 3,3',4,4'-tetrachlorobenzil are reacted analogously to the method according to step I.11.2 to obtain the corresponding benzilic acid. Yield: 42 g of yellowish powder; melting point: 224° C.

I.19.3: methyl 3,3',4,4'-tetrachlorobenzilate 42 g (0.114 mol) of 3,3',4,4'-tetrachlorobenzilic acid are reacted analogously to step I.10.3. Yield: 15.84 g (37% of theory); melting point: 69° C.

I.20: methyl 3,3',4,4',5,5'-hexafluorobenzilate 3t

I.20.1: 3,3',4,4',5,5'-hexafluorobenzil

The reaction to form the acyloin derivative is carried out analogously to the process according to step I.11.1 starting from 31.38 g of 3,4,5-trifluorobenzaldehyde. Yield: 24.92 g.

24.92 g of the acyloin thus obtained are reacted analogously to the method according to step I.11.1 to obtain the benzil. Yield: 14.65 g of yellow crystals.

I.20.2: 3,3',4,4',5,5'-hexafluorobenzilic acid 14,62 g (0.046 mol) of 3,3',4,4',5,5'-hexafluorobenzil are reacted analogously to the method according to step I.11.2 to obtain the corresponding benzilic acid. Yield: 15.77 g of yellow crystals.

I.20.3: methyl 3,3',4,4',5,5'-hexafluorobenzilbenzilate 42 g (0.114 mol) of 3,3',4,4'-tetrachlorobenzilic acid are reacted analogously to step I.10.3. Yield: 5.65 g (35% of theory); melting point: 82° C.–83° C.

II. Synthesis of the Compounds of General Formula 4

II.1: tropenol 3,3',4,4'-tetrafluorobenzilate 4.1

4.27 g (0.013 mol) of ethyl 3,3',4,4'-tetrafluorobenzilate A, 1.81 g (0.013 mol) of tropenol, and 0.03 g of sodium are heated for 4 hours as a melt at 75 mbar over a bath of boiling water with occasional shaking. After cooling, the sodium residues are dissolved with acetonitrile, the solution is evaporated to dryness and the residue is extracted with dichloromethane/water. The organic phase is washed with water, dried over $MgSO_4$, and evaporated to dryness. The residue remaining is combined with diethylether/petroleum ether (1:9), suction filtered, and washed. Yield: 2.50 g (46% of theory); TLC: $R_f$ value: 0.29 (eluant: sec-butanol/formic acid/water 75:15:10); melting point: 147° C.–148° C.

II.2: scopine 3,3',4,4'-tetrafluorobenzilate 4.2

4.2 is prepared analogously to the method according to II.1. Yield: 1.75 g (36% of theory) starting from 3.61 g (0.011 mol) of 3a and 1.71 g (0.011 mol) of scopine; TLC: $R_f$ value: 0.22 (eluant as in step II.1); melting point: 178° C.–179° C.

II.3: tropenol 4,4'-dichlorobenzilate 4.3

4.3 is prepared analogously to the method according to II.1. Yield: 6.95 g (83% of theory) starting from 6.5 g (0.02 mol) of 3i and 2.78 g (0.02 mol) of tropenol; TLC: $R_f$ value: 0.30 (eluant as in step II.1); melting point: 197° C.–199° C.

II.4: tropenol 2,2'-dichlorobenzilate 4.4

4.4 is prepared analogously to the method according to II.1; the product was precipitated as the hydrochloride and recrystallized from acetonitrile. Yield: 1.13 g (8% of theory) starting from 9.3 g (0.03 mol) of 3b and 8.32 g (0.06 mol) of tropenol; TLC: $R_f$ value: 0.26 (eluant as in step II.1); melting point: 253° C.–256° C. (hydrochloride).

II.5: tropenol 4,4'-difluorobenzilate 4.5

4.5 is prepared analogously to the method according to II.1. Yield: 8.71 g (69% of theory) starting from 8.35 g (0.03 mol) of 3c and 4.18 g (0.03 mol) of tropenol; TLC: $R_f$ value: 0.34 (eluant as in step II.1); melting point: 167° C.–169° C.

II.6: tropenol 2,2',4,4'-tetrafluorobenzilate 4.6:

4.6 is prepared analogously to the method according to II.1. Yield: 1.80 g (27% of theory) starting from 4.00 g (0.013 mol) of 3d and 3.54 g (0.036 mol) of tropenol; melting point: 190° C.

II.7: scopine 4,4'-dichlorobenzilate 4.7

3.78 g (0.01 mol) of tropenol 4,4'-dichlorobenzilate 4.3 are suspended in 40 ml of DMF and heated to 60° C. until a clear solution is formed. At an internal temperature of about 40° C., a solution of 1.92 g (0.0216 mol) of $H_2O_2$-urea in 10 ml of water, and 0.183 g (0.0011 mol) of vanadium-(V)-oxide is added and the mixture is stirred for 4.5 hours at 60° C. After cooling to 20° C., the precipitate formed is suction filtered, the filtrate is adjusted to pH 3 with 4 N hydrochloric acid and combined with 0.437 g (0.0023 mol) of $Na_2S_2O_7$ in 10 ml of water. The green solution thus formed is evaporated to dryness, the residue is extracted with dichloromethane/water. The acidic aqueous phase is made basic with $Na_2CO_3$, extracted with dichloromethane, and the organic phase is dried over $Na_2SO_4$ and concentrated. Then 0.5 ml of acetyl chloride is added at about 15° C. and the mixture is stirred for 1.5 hours. After extraction with 0.1 N hydrochloric acid, the aqueous phase is made basic, extracted with dichloromethane; the organic phase is dried over $Na_2SO_4$ and evaporated to dryness. The hydrochloride is precipitated from the residue and recrystallized from methanol/diethylether. Yield: 1.92 g of 18 (45% of theory); TLC: $R_f$ value: 0.29 (eluant as in II.1); melting point: 238° C.–239° C. (hydrochloride).

II.8: scopine 4,4'-difluorobenzilate 4.8

4.8 is prepared analogously to the method according to II.7. Yield: 2.60 g (70% of theory) starting from 3.27 g (0.09 mol) of 4e; TLC: $R_f$ value: 0.25 (eluant as in step II.1); melting point: 243° C.–244° C. (hydrochloride).

II.9: tropenol 4,4'-dibromobenzilate 4.9

4.9 is prepared analogously to the method according to II.1. Yield: 2.36 g (19% of theory) starting from 9.9 g (0.023 mol) of commercially obtainable isopropyl 4,4'-dibromobenzilate and 3.21 g (0.023 mol) of tropenol; to purify it, the hydrochloride was precipitated and recrystallized from acetonitrile. TLC: $R_f$ value: 0.30 (eluant as in step II.1); melting point: 205° C.–207° C. (hydrochloride).

II.10: tropenol 4,4'-dimethylbenzilate 4.10

4.10 is prepared analogously to the method according to II.1. Yield: 3.55 g (81% of theory) starting from 2.87 g (0.01 mol) of 3& and 1.48 g (0.01 mol) of tropenol; to purify it, the hydrochloride was precipitated and recrystallized from acetonitrile. Melting point: 232° C.–233° C. (hydrochloride).

II.11: scopine 4,4'-dimethylbenzilate 4.11

4.11 is prepared analogously to the method according to II.1. Yield: 1.02 g (24% of theory) starting from 2.87 g (0.01 mol) of 31 and 1.65 g (0.01 mol) of scopine; to purify it, the hydrochloride was precipitated. Melting point: 181° C.–183° C. (hydrochloride).

II.12: tropine 3,3',4,4'-tetrafluorobenzilate 4.12

4.12 is prepared analogously to the method according to II.1. Yield: 2.35 g (53% of theory) starting from 3.45 g (0.01 mol) of 3a and 1.49 g (0.01 mol) of tropine; melting point: 142° C.–144° C.

II.13: tropenol 3,3',4,4'-tetramethoxybenzilate 4.13

2.60 g (0.007 mol) of 3f, 1.00 g (0.007 mol) of tropenol and 0.03 g of sodium are placed in 15 ml of toluene and refluxed for 4 hours. After cooling, the mixture is diluted with about 100 ml of toluene and extracted with water; the organic phase is dried over $MgSO_4$ and evaporated to dryness. Yield: 1.60 g of oil (47% of theory).

II.14: tropenol 4,4'-dimethoxybenzilate 4.14

4.14 is prepared analogously to the method according to II.1. Yield: 3.3 g (78% of theory) starting from 3.0 g (0.01 mol) of 3g and 1.39 g (0.01 mol) of tropenol; melting point: 146° C.–147° C.

II.15: tropine 3,3',4,4'-tetramethoxybenzilate 4.15

4.15 is prepared analogously to the method according to II.1. Yield: 1.65 g (32% of theory; oil) starting from 4.0 g (0.02 mol) of 3f and 3.12 g (0.02 mol) of tropine.

II.16: scopine 3,3',4,4'-tetramethoxybenzilate 4.16

4.16 is prepared analogously to the method according to II.7. Yield: 0.8 g (41% of theory, oil) starting from 1.857 g (0.004 mol) of 413.

II.17: tropenol 3,3'-dimethyl-4,4'-dimethoxybenzilate 4.17

4.17 is prepared analogously to the method according to II.1; the product is purified by recrystallizing from diethyl-ether. Yield: 2.30 g (35% of theory) starting from 5.0 g (0.015 mol) of 3h and 4.21 g (0.03 mol) of tropenol; melting point: 126° C.

II.18: scopine 3,3'-dimethyl-4,4'-dimethoxybenzilate 4.18

4.18 is prepared analogously to the method according to II.7. Yield: 0.6 g (44% of theory, oil) starting from 1.3 g (0.003 mol) of 4q.

II.19: tropenol 3,3',5,5'-tetrafluorobenzilate 4.19

1.53 g (0.0636 mol) of NaH are placed in 30 ml of toluene, a solution of 14 g (0.0446 mol) of 3j and 8.85 g (0.0636 mol) of tropenol in 80 ml of toluene is added dropwise at 10° C. and 860 mbar. The alcohol produced during the reaction is distilled off while at the same time toluene is added dropwise. After 3 hours, the mixture is cooled and extracted, with dichloromethane and water. The combined organic phases were dried over $MgSO_4$ and evaporated to dryness. The residue was stirred with petroleum ether/ethyl acetate 95:5. Yield: II.21 g of light beige crystals (60% of theory); melting point: 168° C.–170° C.

II.20: scopine 2,2',4,4'-tetrafluorobenzilate 4.20

The preparation of 4.20 is carried out analogously to the process according to II.7. Yield: 1.05 g of white crystals (89% of theory) starting from 1.15 g (0.0027 mol) of 4.

II.21: scopine 3,3',5,5'-tetrafluorobenzilate 4.21

The preparation of 4.21 is carried out analogously to the process according to II.7. Yield: 1.13 g of white crystals (55% of theory) starting from 2.0 g (0.0047 mol) of 4.19; melting point: 199° C.–200° C.

II.22: tropenol 3,3'-dichlorobenzilate 4.22

22.9 g (0.074 mol) of methyl 3,3'-dichlorobenzilate 3k, 15.37 g (0.11 mol) of tropenol, and 0.17 g of sodium are heated for 4 hours as a melt over a bath of boiling water at 75 mbar with occasional shaking. After cooling, the sodium residues are dissolved with acetonitrile, the solution is evaporated to dryness and the residue is extracted with dichloromethane/water. The organic phase is washed with water, dried over $MgSO_4$, and evaporated to dryness. The product is recrystallized from acetonitrile in the form of its hydrochloride. Yield: 16.83 g of white crystals (50% of theory); melting point: 184° C.–185° C.

II.23: troplenol 4,4'-di(trifluoromethyl)benzilate 4.23

Starting from 10.0 g (0.0264 mol) of 3l the reaction is carried out analogously to step II.1. Yield: 4.70 g of beige crystals (37% of theory); melting point: 155° C.

II.24: tropenol 3,3'-di(trifluoromethyl)benzilate 4.24

Starting from 6.01 g (0.0159 mol) of 3m the reaction is carried out analogously to step II.1. Yield: 3.03 g of white crystals (39% of theory); melting point: 124° C.–125° C.

II.25: scopine 4,4'-di(trifluoromethyl)benzilate 4.25

The preparation of 4.25 is carried out analogously to the process according to II.7. Yield: 0.95 g of clear oil (46% of theory) starting from 2.0 g (0.0041 mol) of 4.23.

II.26: scopine 3,3'-di(trifluoromethyl)benzilate 4.26

The preparation of 42 is carried out analogously to the process according to II.7. Yield: 1.02 g of white crystals (51% of theory) starting from 1.94 g (0.0039 mol) of A.

II.27: tropenol 3,3'-dichloro-4,4'-difluorobenzilate 4.27

Starting from 6.77 g (0.0195 mol) of 3n the reaction is carried out analogously to step II.1. The crude product obtained is recrystallized from acetonitrile. Yield: 4.05 g of light beige crystals (46% of theory); melting point: 177° C.–179° C.

II.28: scopine 3,3'-dichlorobenzilate 4.28

The preparation of 4.28 is carried out analogously to the process according to II.7. Yield: 7.86 g (75% of theory) starting from 10.37 g (0.024 mol) of A; melting point: 174° C.–175° C.

II.29: tropenol 2,2',5,5'-tetrafluorobenzilate 4.29

Starting from 6.29 g (0.02 mol) of 3o the reaction is carried out analogously to step I.11. The crude product obtained is recrystallized from acetone in the form of the hydrochloride. Yield: 0.89 g of white crystals (10% of theory); melting point: 177° C.–179° C.

II.30: tropenol 2,2',3,3'-tetrafluorobenzilate 4.30

Starting from 8.0 g (0.0255 mol) of the reaction is carried out analogously to step II.1. The crude product obtained is recrystallized from acetonitrile. Yield: 0.96 g of beige crystals (9% of theory); melting point: 176° C.–177° C.

II.31: tropenol 3,3'-difluorobenzilate 4.31

Starting from II.13 g (0.04 mol) of 3q the reaction is carried out analogously to step I.1. The crude product obtained is recrystallized from acetonitrile in the form of the hydrochloride. Yield: 7.98 g (47% of theory); melting point: 245° C.–246° C.

II.32: scopine 3,3'-difluorobenzilate 4.32

The preparation of 4.32 is carried out analogously to the process according to II.7. Yield: 4.2 g (76% of theory) starting from 4.89 g (0.013 mol) of 4.31; melting point: 216° C.–218° C.

II.33: scopine 3,3'-dichloro-4,4'-difluorobenzilate 4.33

The preparation of 433 is carried out analogously to the process according to II.7. Yield: 0.78 g of white crystals (34% of theory) starting from 4.6 g (0.0098 mol) of 4.27; melting point: 216° C.–218° C.

II.34: tropenol 4,4'-dichloro-3,3'-difluorobenzilate 4.34

Starting from 12.0 g (0.0345 mol) of 3r the reaction is carried out analogously to step II.1. The crude product obtained is extracted from petroleum ether. Yield: 6.65 g of creamy-white powder (42% of theory); melting point: 180° C.–181° C.

II.35: scopine 4,4'-dichloro-3,3'-difluorobenzilate 4.35

The preparation of 4.35 is carried out analogously to the process according to II.7. Yield: 2.58 g of white crystals (62% of theory) starting from 4.0 g (0.0088 mol) of 4.34; melting point: 150° C.–151° C.

II.36: tropenol 3,3',4,4'-tetrachlorobenzilate 4.36

Starting from 14.24 g (0.0375 mol) of 3s the reaction is carried out analogously to step II.1. The crude product obtained is recrystallized from acetonitrile. Yield: 4.81 g of white crystals (26% of theory); melting point: 149° C.–150° C.

II.37: tropenol 3,3',4,4',5,5'-hexafluorobenzilate 4.37

Starting from 5.0 g (0.0143 mol) of 3t the reaction is carried out analogously to step II.1. The crude product obtained is recrystallized from acetonitrile. Yield: 3.49 g of white crystals (53% of theory); melting point: 164° C.–165° C.

III. Synthesis of the Compounds of General Formula 1

EXAMPLE 1 tropenol 3,3',4,4'-tetrafluorobenzilate methobromide

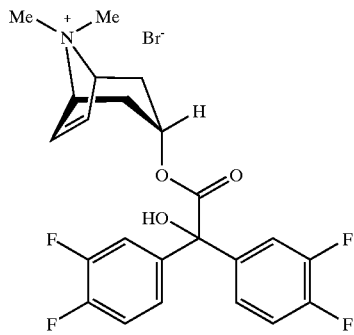

2.00 g (0.0048 mol) of 4.1, 30 ml of acetonitrile, 10 ml of dichloromethane, and 2.88 g (0.0143 mol) of 46.92% bromomethane in acetonitrile are combined at 20° C. and left to stand for 3 days. The solution is evaporated to dryness and the residue is recrystallized from acetonitrile. Yield: 1.95 g (80% of theory); TLC: $R_f$ value: 0.12 (eluant as in step II.1); melting point: 238° C.; $C_{23}H_{22}F_4NO_3xBr$ (516.33);

| Elemental analysis: | calculated: | C (53.50) | H (4.29) | N (2.71) |
|---|---|---|---|---|
| | found: | C (53.52) | H (4.30) | N (2.65). |

EXAMPLE 2 scopine 3,3',4,4'-tetrafluorobenzilate methobromide

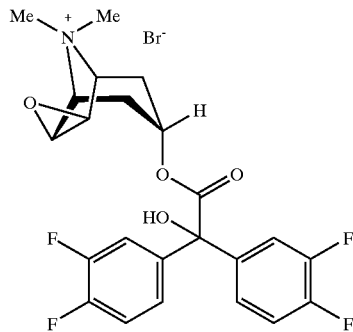

1.5 g (0.0034 mol) of 4.2, 20 ml of acetonitrile, 20 ml of dichloromethane, and 2.08 g (0.01 mol) of 46.92% bromomethane in acetonitrile are reacted analogously to Example 1. Yield: 1.40 g (77% of theory); TLC: $R_f$ value: 0.16 (eluant as in step II.1); melting point: 227° C.; $C_{23}H_{22}F_4NO_4xBr$ (532.33).

| Elemental analysis: | calculated: | C (51.90) | H (4.17) | N (2.63) |
|---|---|---|---|---|
| | found: | C (51.91) | H (4.16) | N (2.60). |

EXAMPLE 3 tropenol 4,4'-dichlorobenzilate methobromide

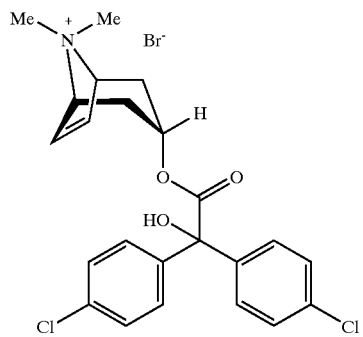

2.09 g (0.005 mol) of 4.3 are reacted analogously to Example 1. The crystals formed are suction filtered, washed with dichloromethane, dried, and then recrystallized from methanol/diethylether. Yield: 1.72 g (67% of theory); TLC: $R_f$ value: 0.12 (eluant as in step II.1); melting point: 195° C.–196° C.; $C_{23}H_{24}Cl_2NO_3xBr$ (513.26).

| Elemental analysis: | calculated: | C (53.82) | H (4.71) | N (2.73) |
|---|---|---|---|---|
| | found: | C (53.54) | H (4.80) | N (2.73). |

EXAMPLE 4 tropenol 2,2'-dichlorobenzilate methobromide

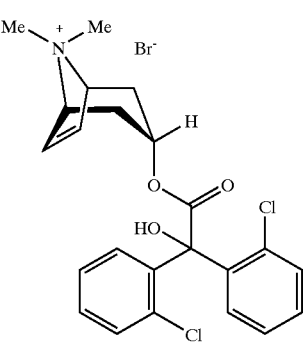

0.86 g (0.0021 mol) of the free base of 4.4 are reacted analogously to Example 1. The crystals formed are suction filtered, washed with acetone, dried, and then recrystallized from methanol/diethylether. Yield: 0.99 g (94% of theory); TLC: $R_f$ value: 0.14 (eluant as in step II.1); melting point: 260° C.–261° C.; $C_{23}H_{24}Cl_2NO_3xBr$ (513.26).

| Elemental analysis: | calculated: | C (53.82) | H (4.71) | N (2.73) |
|---|---|---|---|---|
| | found: | C (53.62) | H (4.76) | N (2.69). |

EXAMPLE 5 tropenol 4,4'-difluorobenzilate methobromide

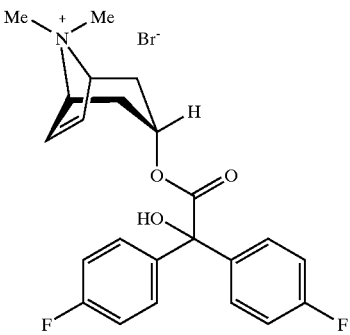

1.9 g (0.005 mol) of the free base of 4.5 are reacted analogously to Example 1. Yield: 2.1 g (89% of theory); TLC: $R_f$ value: 0.14 (eluant as in step II.1); melting point: 219° C.–220° C.; $C_{23}H_{24}F_2NO_3xBr$ (480.35).

| Elemental analysis: | calculated: | C (57.51) | H (5.04) | N (2.92) |
|---|---|---|---|---|
| | found: | C (57.33) | H (4.86) | N (2.90). |

EXAMPLE 6 tropenol 2,2',4,4'-tetrafluorobenzilate methobromide

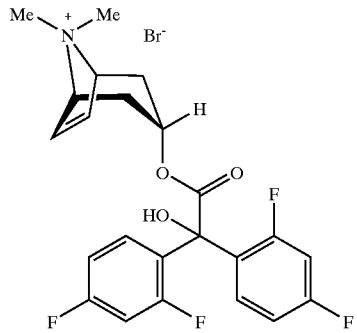

1.60 g (0.004 mol) of 4.6 are reacted analogously to Example 1. The crystals formed are suction filtered and recrystallized from acetone. Yield: 1.70 g (87% of theory); TLC: $R_f$ value: 0.13 (eluant: n-butanol/water/formic acid (conc.)/acetone/dichloromethane 36:15:15:15:5); melting point: 241° C.–242° C.; $C_{23}H_{22}F_4NO_3xBr$ (516.33).

| Elemental analysis: | calculated: | C (53.50) | H (4.29) | N (2.71) |
| --- | --- | --- | --- | --- |
| | found: | C (53.55) | H (4.33) | N (2.73). |

EXAMPLE 7 scopine 4,4'-dichlorobenzilate methobromide

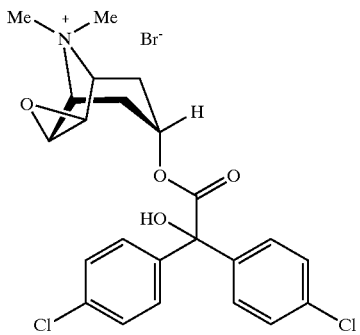

1.54 g (0.0035 mol) of the free base of 4.7 are reacted analogously to Example 1. The crystals formed are suction filtered, washed with acetone, dried, and then recrystallized from methanol/diethylether. Yield: 1.68 g (90% of theory); TLC: $R_f$ value: 0.22 (eluant as in step II.1); melting point: 209° C.–210° C.; $C_{23}H_{24}Cl_2NO_4xBr$ (529.26).

| Elemental analysis: | calculated: | C (52.20) | H (4.57) | N (2.65) |
| --- | --- | --- | --- | --- |
| | found: | C (51.25) | H (4.83) | N (2.49). |

EXAMPLE 8 scopine 4,4'-difluorobenzilate methobromide

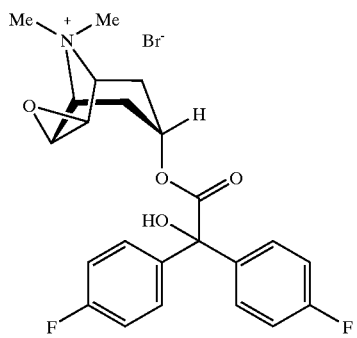

1.50 g (0.003 mol) of the free base of 4.8 are reacted analogously to Example 1. The crystals formed are suction filtered, washed with acetone, dried, and then recrystallized from methanol/diethylether. Yield: 1.73 g (93% of theory); TLC: $R_f$ value: 0.19 (eluant as in step II.1); melting point: 224° C.–225° C.; $C_{23}H_{24}F_2NO_4xBr$ (496.35).

| Elemental analysis: | calculated: | C (55.66) | H (4.87) | N (2.82) |
| --- | --- | --- | --- | --- |
| | found: | C (55.20) | H (4.81) | N (282). |

EXAMPLE 9 tropenol 2,2',4,4'-tetrafluorobenzilate methobromide

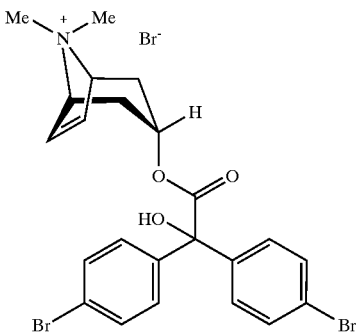

1.50 g (0.003 mol) of the free base of 4.9 are reacted analogously to Example 1. The crystals formed are recrystallized from methanol. Yield: 1.53 g (86% of theory); TLC: $R_f$ value: 0.14 (eluant as in step II.1); melting point: 175° C.–177° C.; $C_{23}H_{24}Br_2NO_3xBr$ (602.16).

| Elemental analysis: | calculated: | C (45.88) | H (4.02) | N (2.33) |
| --- | --- | --- | --- | --- |
| | found: | C (45.46) | H (4.42) | N (2.18). |

EXAMPLE 10 tropenol 4,4'-dimethylbenzilate methobromide

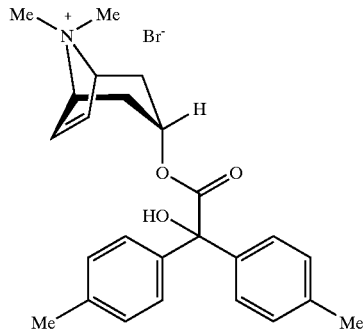

2.60 g (0.007 mol) of the free base of 4.10 are reacted analogously to Example 1. The crystals formed are recrystallized from ethanol. Yield: 3.16 g (97% of theory); TLC: $R_f$ value: 0.14 (eluant as in step II.1); $C_{25}H_{30}NO_3xBr$ (472.42).

| Elemental analysis: | calculated: | C (63.56) | H (6.40) | N (2.96) |
|---|---|---|---|---|
| | found: | C (62.88) | H (6.87) | N (2.74). |

EXAMPLE 11 scopine 4,4'-dimethylbenzilate methobromide

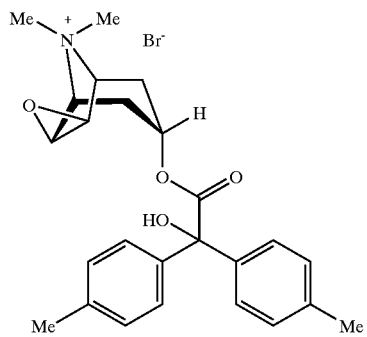

0.56 g (0.0014 mol) of the free base of 4.11 are reacted analogously to Example 1. The crystals formed are recrystallized from methanol/diethylether. Yield: 0.55 g (80% of theory); TLC: $R_f$ value: 0.19 (eluant as in step II.1); melting point: 221° C.–222° C.; $C_{25}H_{30}NO_4xBr$ (488.42).

| Elemental analysis: | calculated: | C (61.48) | H (6.19) | N (2.87) |
|---|---|---|---|---|
| | found: | C (60.61) | H (6.31) | N (2.80). |

EXAMPLE 12 tropine 3,3',4,4'-tetrafluorobenzilate methobromide

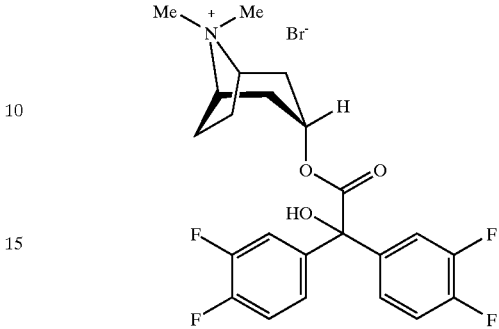

1.80 g (0.004 mol) of the free base of 4.12 are reacted analogously to Example 1. Yield: 1.73 g (78% of theory); TLC: $R_f$ value: 0.10 (eluant as in step II.1); melting point: 157° C.; $C_{23}H_{24}F_4NO_3xBr$ (518.34).

| Elemental analysis: | calculated: | C (53.30) | H (4.67) | N (2.70) |
|---|---|---|---|---|
| | found: | C (53.39) | H (4.53) | N (2.73). |

EXAMPLE 13 tropenol 3,3',4,4'-tetramethoxybenzilate methobromide

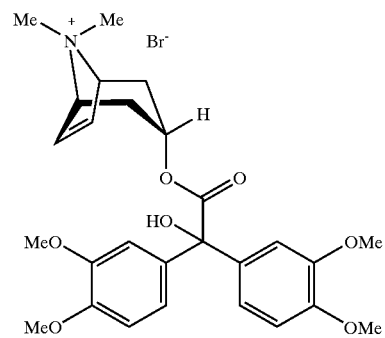

1.20 g (0.003 mol) of 4.13 are reacted analogously to Example 1. The crystals formed are recrystallized from acetonitrile/diethylether. Yield: 1.05 g (73% of theory); TLC: $R_f$ value: 0.10 (eluant as in step II.1); melting point: 212° C.; $C_{27}H_{34}NO_7xBr$ (564.47);

| Elemental analysis: | calculated: | C (57.45) | H (6.07) | N (2.48) |
|---|---|---|---|---|
| | found: | C (56.91) | H (6.05) | N (2.45). |

EXAMPLE 14 tropenol 4,4'-dimethoxybenzilate methobromide

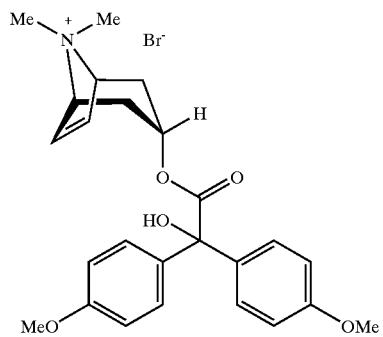

1.13 g (0.003 mol) of 4.14 are reacted analogously to Example 1. The crystals formed are recrystallized from acetonitrile/diethylether. Yield: 1.21 g (87% of theory); $C_{25}H_{30}NO_5xBr$ (504.42); TLC: $R_f$ value: 0.01 (eluant as in step II.1); melting point: 180° C.–181° C.

| Elemental analysis: | calculated: | C (59.53) | H (5.99) | N (2.78) |
|---|---|---|---|---|
| | found: | C (59.29) | H (6.24) | N (2.84). |

EXAMPLE 15 tropine 3,3',4,4'-tetramethoxybenzilate methobromide

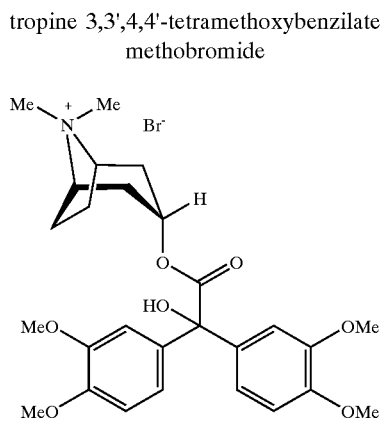

1.65 g (0.004 mol) of 4.15 are reacted analogously to Example 1. The crystals formed are recrystallized from diethylether. Yield: 1.70 g (86% of theory); melting point: 148° C.–150° C.; $C_{27}H_{36}NO_7xBr$ (566.49).

| Elemental analysis: | calculated: | C (57.25) | H (6.41) | N (2.47) |
|---|---|---|---|---|
| | found: | C (56.41) | H (6.75) | N (2.45). |

EXAMPLE 16 scopine 3,3',4,4'-tetramethoxybenzilate methobromide

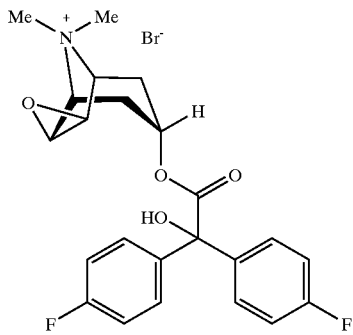

0.80 g (0.0017 mol) of 4.16 are reacted analogously to Example 1. The crystals formed are recrystallized from acetone. Yield: 0.35 g (37% of theory); melting point: 211° C.–212° C.; $C_{27}H_{34}NO_8xBr$ (580.47).

| Elemental analysis: | calculated: | C (55.87) | H (5.90) | N (2.41) |
|---|---|---|---|---|
| | found: | C (55.62) | H (6.09) | N (2.53). |

EXAMPLE 17 tropenol 3,3'-dimethyl-4,4'-dimethoxybenzilate methobromide

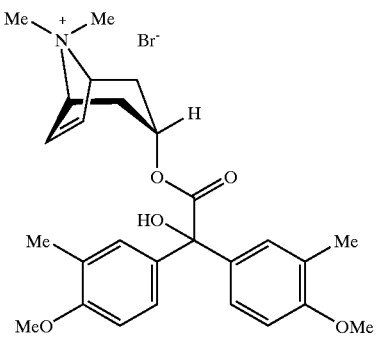

1.00 g (0.003 mol) of 4.17 are reacted analogously to Example 1. Yield: 0.85 g (70% of theory); melting point: 217° C.; $C_{27}H_{34}NO_5xBr$ (532.47).

| Elemental analysis: | calculated: | C (60.90) | H (6.51) | N (2.63) |
|---|---|---|---|---|
| | found: | C (59.83) | H (6.51) | N (2.93). |

EXAMPLE 18 scopine 3,3'-dimethyl-4,4'-dimethoxybenzilate

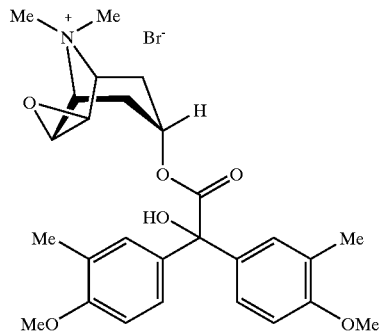

0.60 g (0.0013 mol) of 4.18 are reacted analogously to Example 1. The product is purified by crystallization from acetone. Yield: 0.40 g (56% of theory); $C_{27}H_{34}NO_6 \times Br$ (548.47).

| Elemental analysis: | calculated: | C (59.13) | H (6.25) | N (2.55) |
|---|---|---|---|---|
| | found: | C (58.69) | H (6.54) | N (2.61). |

EXAMPLE 19 tropenol 3,3',4,4'-tetrafluorobenzilate ethylbromide

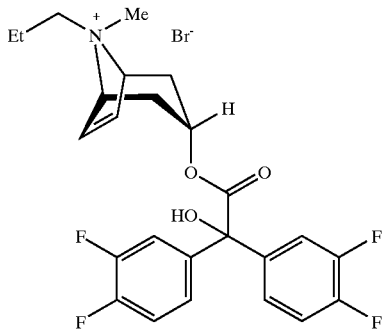

2.00 g (0.0048 mol) of 4.1 is dissolved in 20 ml dichloromethane and 20 ml acetonitrile, combined with 2.59 g (0.0238 mol) of bromoethane and the reaction vessel is sealed. It is left to stand at about 20° C. for 3 weeks with the exclusion of light. The solution is evaporated to dryness and the residue is recrystallized from acetonitrile. Yield: 1.96 g of 3 (78% of theory); TLC: $R_f$ value: 0.11 (eluant as in step II.1); melting point: 247° C.

| Elemental analysis: | calculated: | C (54.35) | H (4.56) | N (2.64) |
|---|---|---|---|---|
| | found: | C (53.93) | H (4.59) | N (2.60). |

EXAMPLE 20 tropenol 3,3',5,5'-tetrafluorobenzilate methobromide

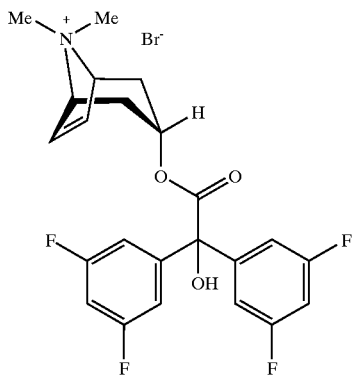

2.0 g (0.0047 mol) of 4.19 are reacted analogously to Example 1. Yield: 2.22 g of white crystals (92% of theory); melting point: 262° C.–264° C.; $C_{23}H_{22}F_4NO_3 \times Br$ (516.33).

| Elemental analysis: | calculated: | C (53.50) | H (4.29) | N (2.71) |
|---|---|---|---|---|
| | found: | C (53.48) | H (4.30) | N (2.65). |

EXAMPLE 21 scopine 2,2',4,4'-tetrafluorobenzilate methobromide

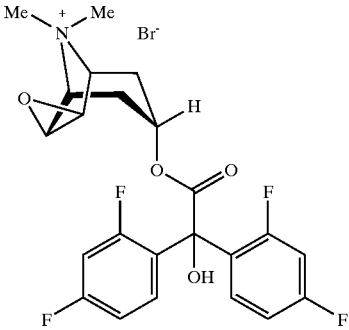

1.05 g (0.0024 mol) of 4.20 are reacted analogously to Example 1. Yield: 0.54 g of white crystals (42% of theory); melting point: 208° C.–209° C.; $C_{23}H_{22}F_4NO_4 \times Br$ (532.33).

| Elemental analysis: | calculated: | C (51.90) | H (4.17) | N (2.63) |
|---|---|---|---|---|
| | found: | C (50.84) | H (4.39) | N (2.50). |

EXAMPLE 22 scopine 3,3',5,5'-tetrafluorobenzilate methobromide

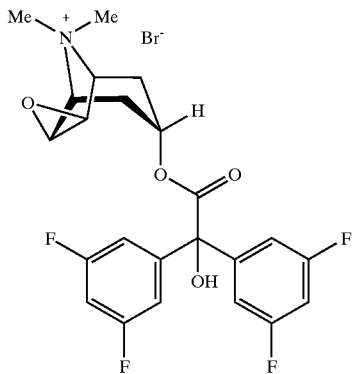

1.13 g (0.00258 mol) of 4.21 are reacted analogously to Example 1. Yield: 1.07 g of white crystals (78% of theory); melting point: 238° C.–239° C.; $C_{23}H_{22}F_4NO_4xBr$ (532.33).

| Elemental analysis: | calculated: | C (51.90) | H (4.17) | N (2.63) |
|---|---|---|---|---|
| | found: | C (51.85) | H (4.29) | N (2.70). |

EXAMPLE 23 tropenol 3,3'-dichlorobenzilate methobromide

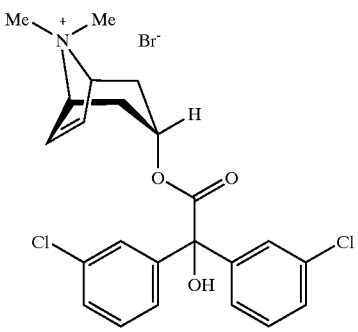

2.09 g (0.005 mol) of 4.22 are reacted analogously to Example 1. Yield: 2.42 g of white crystals (94% of theory); melting point: 200° C.–201° C.; $C_{23}H_{24}Cl_2NO_3xBr$ (513.26).

| Elemental analysis: | calculated: | C (53.82) | H (4.71) | N (2.73) |
|---|---|---|---|---|
| | found: | C (53.73) | H (4.74) | N (2.78). |

EXAMPLE 24 tropenol 4,4'-di(trifluoromethyl)benzilate methobromide

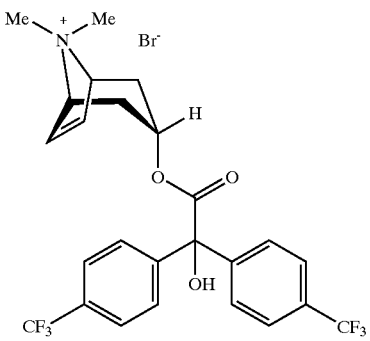

1.2 g (0.00247 mot) of 4.23 are reacted analogously to Example 1. Yield: 1.05 g of white crystals (73% of theory); melting point: 140° C.–141° C.; $C_{25}H_{24}F_6NO_3xBr$ (580.36).

EXAMPLE 25 tropenol 3,3'-di(trifluoromethyl)benzilate methobromide

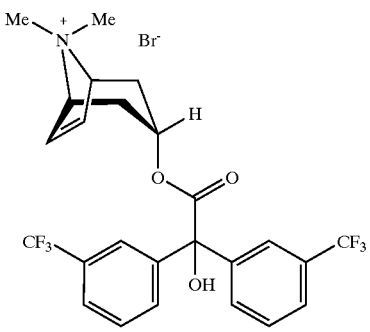

1.09 g (0.00225 mol) of 4.24 are reacted analogously to Example 1. Yield: 0.84 g of white crystals (65% of theory); melting point: 228° C.–229° C.; $C_{25}H_{24}F_6NO_3xBr$ (580.36).

| Elemental analysis: | calculated: | C (51.74) | H (4.17) | N (2.41) |
|---|---|---|---|---|
| | found: | C (51.40) | H (4.24) | N (2.42). |

EXAMPLE 26 scopine 4,4'-di(trifluoromethyl)benzilate methobromide

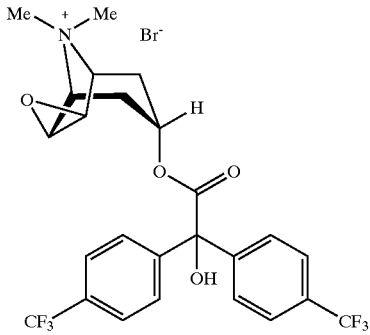

0.95 g (0.0019 mol) of 4.25 are reacted analogously to Example 1. The product is recrystallized from diethylether. Yield: 0.98 g of white crystals (87% of theory); melting point: 158° C.–160° C.; $C_{25}H_{24}F_6NO_4xBr$ (596.36).

| Elemental analysis: | calculated: | C (50.35) | H (4.06) | N (2.35) |
|---|---|---|---|---|
| | found: | C (50.34) | H (4.03) | N (2.36). |

EXAMPLE 27 scopine 3,3'-di(trifluoromethyl)benzilate methobromide

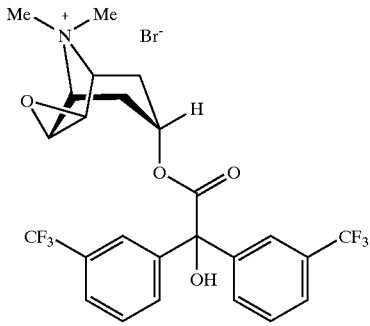

1.0 g (0.002 mol) of 4.26 are reacted analogously to Example 1. The product is recrystallized from acetonitrile. Yield: 0.7 g of white crystals (59% of theory); melting point: 220° C.–221° C.; $C_{25}H_{24}F_6NO_4xBr$ (596.36).

| Elemental analysis: | calculated: | C (50.35) | H (4.06) | N (2.35) |
|---|---|---|---|---|
| | found: | C (50.24) | H (4.17) | N (2.40). |

EXAMPLE 28 tropenol 4,4'-difluorobenzilate ethyl bromide

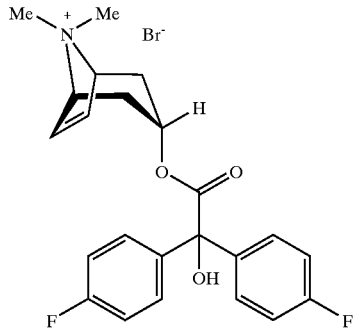

1.54 g (0.004 mol) of 4.5 are reacted analogously to Example 19. The product is recrystallized from ethanol. Yield-1.72 g of white crystals (87% of theory); melting point: 228° C.–229° C.; $C_{24}H_{26}F_2NO_3xBr$ (494.37).

| Elemental analysis: | calculated: | C (58.31) | H (5.30) | N (2.83) |
|---|---|---|---|---|
| | found: | C (58.25) | H (5.29) | N (2.83). |

EXAMPLE 29 tropenol 3,3'-dichloro-4,4'-difluorobenzilate methobromide

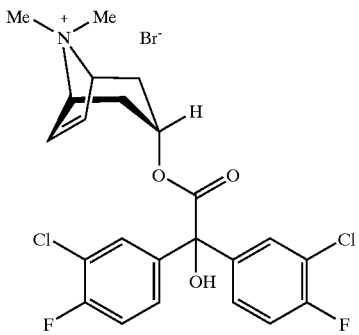

1.5 g (0.0033 mol) of 4.27 are reacted analogously to Example 1. The product is recrystallized from acetonitrile. Yield: 1.49 g of white crystals (82% of theory); melting point: 245° C.–246° C.; $C_{23}H_{22}Cl_2F_2NO_3xBr$ (549.24).

| Elemental analysis: | calculated: | C (50.30) | H (4.04) | N (2.55) |
|---|---|---|---|---|
| | found: | C (50.44) | H (4.19) | N (2.51). |

EXAMPLE 30 scopine 3,3'-dichlorobenzilate methobromide

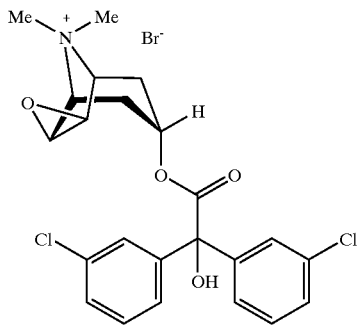

2.61 g (0.006 mol) of 4.28 are reacted analogously to Example 1. The product is recrystallized from ethanol. Yield: 2.13 g of white crystals (67% of theory); melting point: 221° C.–222° C.; $C_{23}H_{24}Cl_2NO_4xBr$ (529.26).

| Elemental analysis: | calculated: | C (52.20) | H (4.57) | N (2.65) |
|---|---|---|---|---|
| | found: | C (52.25) | H (4.61) | N (2.70). |

EXAMPLE 31

2, tropenol 2',5,5'-tetrafluorobenzilate methobromide

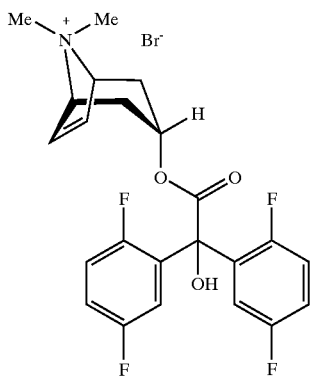

0.67 g (0.0016 mol) of 4.29 are reacted analogously to Example 1. The product is recrystallized from methanol/diethylether. Yield: 0.70 g of white crystals (86% of theory); melting point: 269° C.–270° C.; $C_2H_{22}F_4NO_3xBr$ (516.33).

| Elemental analysis: | calculated: | C (53.50) | H (4.29) | N (2.71) |
|---|---|---|---|---|
| | found: | C (53.30) | H (4.52) | N (2.76). |

EXAMPLE 32

2, tropenol 2',3,3'-tetrafluorobenzilate methobromide

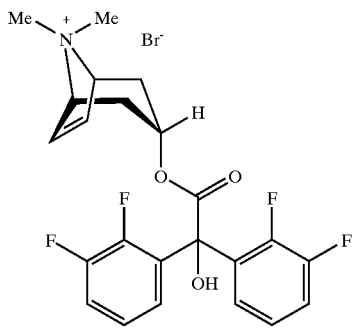

0.96 g (0.002 mol) of 4.30 are reacted analogously to Example 1. The product is recrystallized from acetonitrile. Yield: 0.61 g of white crystals (59% of theory); melting point: 268° C.–269° C.; $C_{23}H_{22}F_4NO_3xBr$ (516.33).

| Elemental analysis: | calculated: | C (53.50) | H (4.29) | N (2.71) |
|---|---|---|---|---|
| | found: | C (53.56) | H (4.38) | N (2.75). |

EXAMPLE 33 scopine 4,4'-difluorobenzilate ethyl bromide

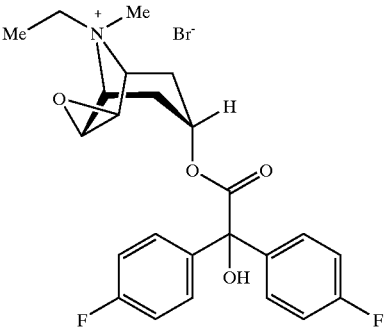

1.2 g (0.003 mol) of 4.8 are reacted analogously to Example 19. The product is recrystallized from ethanol. Yield: 0.93 g of white crystals (61% of theory); melting point: 162° C.–163° C.; $C_{24}H_{26}F_2NO_4xBr$ (510.38).

| Elemental analysis: | calculated: | C (56.48) | H (5.13) | N (2.74) |
|---|---|---|---|---|
| | found: | C (55.96) | H (5.30) | N (2.75). |

EXAMPLE 34 tropenol 3,3'-difluorobenzilate methobromide

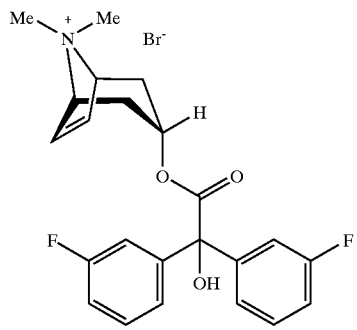

1.61 g (0.004 mol) of 4.31 are reacted analogously to Example 1. The product is recrystallized from ethanol/diethylether. Yield: 1.93 g of white crystals (96% of theory); melting point: 227° C.–228° C.; $C_{23}H_{24}F_2NO_3 \times Br$ (480.35).

| Elemental analysis: | calculated: | C (57.51) | H (5.04) | N (2.92) |
|---|---|---|---|---|
| | found: | C (57.38) | H (5.14) | N (2.95). |

EXAMPLE 35 scopine 3,3'-difluorobenzilate methobromide

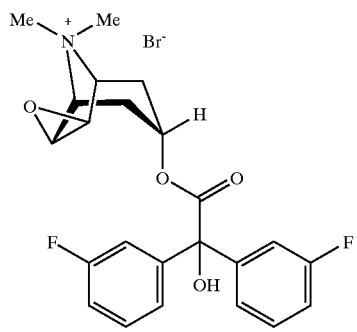

1.61 g (0.004 mol) of 4.32 are reacted analogously to Example 1. The product is recrystallized from ethanol. Yield: 1.83 g of white crystals (92% of theory); melting point: 221° C.–222° C.; $C_{23}H_{24}F_2NO_4 \times Br$ (496.35).

| Elemental analysis: | calculated: | C (55.66) | H (4.87) | N (2.82) |
|---|---|---|---|---|
| | found: | C (55.49) | H (4.78) | N (2.73). |

EXAMPLE 36 scopine 3,3'-dichloro-4,4'-difluorobenzilate methobromide

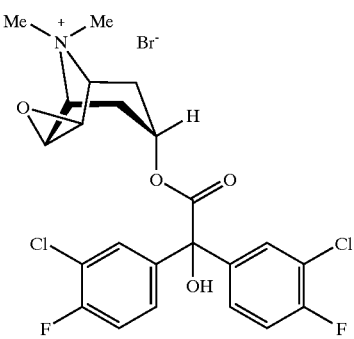

0.78 g (0.002 mol) of 4.33 are reacted analogously to Example 1. The product is recrystallized from acetonitrile. Yield: 0.67 g of white crystals (59% of theory); $C_{23}H_{22}Cl_2F_2NO_4 \times Br$ (565.24).

| Elemental analysis: | calculated: | C (48.87) | H (3.92) | N (2.48) |
|---|---|---|---|---|
| | found: | C (48.87) | H (3.81) | N (2.46). |

EXAMPLE 37 scopine 4,4'-dichloro-3,3'-difluorobenzilate methobromide

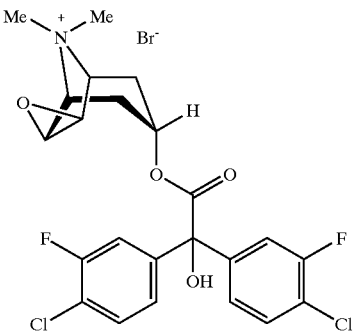

2.4 g (0.0051 mol) of 4.35 are reacted analogously to Example 1. The product is recrystallized from acetonitrile. Yield: 2.45 g of white crystals (85% of theory); melting point: 211° C.–212° C.; $C_{23}H_{22}Cl_2F_2NO_4 \times Br$ (565.24).

EXAMPLE 38 tropenol 3,3',4,4'-tetrachlorobenzilate methobromide

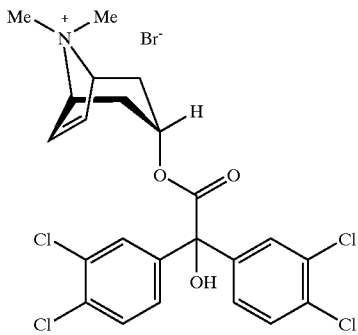

1.8 g (0.00369 mol) of 4.36 are reacted analogously to Example 1. The product is recrystallized from methanol/diethylether. Yield: 2.01 g of white crystals (93% of theory); melting point: 245° C.–246° C.; $C_{23}H_{22}Cl_4NO_3 \cdot xBr$ (582.15).

| Elemental analysis: | calculated: | C (47.45) | H (3.81) | N (2.41) |
|---|---|---|---|---|
| | found: | C (47.27) | H (3.82) | N (2.36). |

EXAMPLE 39 tropenol 4,4'-dichloro-3,3'-difluorobenzilate methobromide

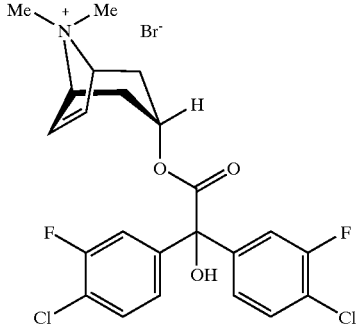

2.5 g (0.0055 mol) of 4.34 are reacted analogously to Example 1. The product is recrystallized from acetonitrile. Yield: 1.53 g of white crystals (51% of theory); melting point: 229° C.–231° C.; $C_{23}H_{22}Cl_2F_2NO_3 \cdot xBr$ (549.24).

EXAMPLE 40 tropenol 3,3',4,4',5,5'-tetrafluorobenzilate methobromide

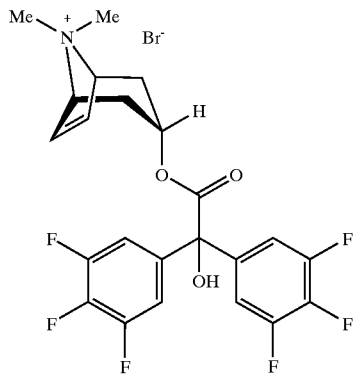

1.7 g (0.0037 mol) of 4.37 are reacted analogously to Example 1. The product is extracted from acetone. Yield: 1.9 g of white crystals (92% of theory); melting point: 241° C.–242° C.; $C_{23}H_{20}F_6NO_3 \cdot xBr$ (552.32).

| Elemental analysis: | calculated: | C (50.02) | H (3.65) | N (2.54) |
|---|---|---|---|---|
| | found: | C (50.09) | H (3.61) | N (2.49). |

As has been found, the compounds of general formula 1 are characterized by their versatility in therapeutic use. Particular mention should be made of those applications for which the compounds of formula 1 according to the invention are preferably used on the basis of their pharmaceutical activity as anticholinergic agents.

These include, for example, the treatment of asthma or COPD (chronic obstructive pulmonary disease). The compounds of general formula 1 may also be used to treat vagally induced sinus bradycardia and to treat heart rhythm disorders. In general, the compounds according to the invention may also be used to treat spasms, e.g., in the gastrointestinal tract, with therapeutic benefit. They may also be used in the treatment of spasms in the urinary tract and in menstrual disorders, for example.

Of the ranges of indications mentioned above, the treatment of asthma and COPD using the compounds of formula 1 according to the invention is of particular importance.

The compounds of general formula 1 may be used on their own or combined with other active substances of formula 1 according to the invention.

The compounds of general formula 1 may optionally also be combined with other pharmacologically active substances. These include, in particular, betamimetics, antiallergic agents, PAF-antagonists, leukotriene-antagonists, and corticosteroids, and combinations of these active substances.

Examples of betamimetics which may be used in conjunction with the compounds of formula 1 according to the invention include compounds selected from among bambuterol, bitolterol, carbuterol, clenbuterol, fenoterol, formoterol, hexoprenaline, ibuterol, pirbuterol, procaterol, reproterol, salmeterol, sulfonterol, terbutaline, tulobuterol, 4-hydroxy-7-[2-{[2-{[3-(2-phenylethoxy)propyl] sulfonyl}ethyl]-amino}ethyl]-2(3H)-benzothiazolone, 1-(2-fluoro-4-hydroxyphenyl)-2-[4-(1-benzimidazolyl)-2- methyl-2-butylamino)ethanol, 1-[3-(4-methoxybenzyl-amino)₄-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-on, 1-(4-amino-3-chloro-5-trifluoromethylphenyl)-2-tert-butylamino)ethanol, and 1-(4-ethoxycarbonylamino-3-cyano-5-fluorophenyl)-2-(tert-butylamino)ethanol, optionally in the form of their racemates, their enantiomers, their diastereomers, as well as optionally their pharmacologically acceptable acid addition salts and hydrates. It is particularly preferable to use, as betamimetics, active substances of this kind, combined with the compounds of formula 1 according to the invention, selected from among fenoterol, formoterol, salmeterol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-41,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-(2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-9-yl]-2-{4[3-(4-methoxyphenyl)-1,2,4-triazol-3-yl]-2-methyl-2-butylamino}ethanol, optionally in the form of their racemates, their enantiomers, their diastereomers, as well as optionally their pharmacologically acceptable acid addition salts and hydrates. Of the betamimetics mentioned above, the compounds formoterol and salmeterol, optionally in the form of their racemates, their enantiomers, their diastereomers, as well as optionally their pharmacologically acceptable acid addition salts and hydrates, are particularly important.

The acid addition salts of the betamimetics selected from among the hydrochloride, hydrobromide, sulfate, phosphate, fumarate, methanesulfonate, and xinafoate are preferred according to the invention. In the case of salmeterol, the salts selected from among the hydrochloride, sulfate, and xinafoate are particularly preferred, especially the sulfates and xinafoates. Of outstanding importance according to the invention are salmeterol×½$H_2SO_4$ and salmeterol xinafoate. In the case of formoterol, the salts selected from among the hydrochloride, sulfate, and fumarate are particularly preferred, especially the hydrochloride and fumarate. Of outstanding importance according to the invention is formoterol fumarate.

Within the scope of the present invention, the term corticosteroids, which is optionally used in conjunction with the compounds of formula 1, denotes compounds selected from among flunisolide, beclomethasone, triamcinolone, budesonide, fluticasone, mometasone, ciclesonide, rofleponide, GW 215864, KSR 592, ST-126 and dexamethasone. The preferred corticosteroids within the scope of the present invention are those selected from among flunisolide, beclomethasone, triamcinolone, budesonide, fluticasone, mometasone, ciclesonide, and dexamethasone, while budesonide, fluticasone, mometasone, and ciclesonide, especially budesonide and fluticasone, are of particular importance. The term steroids may be used on its own, within the scope of the present patent application, instead of the term corticosteroids. Any reference to steroids within the scope of the present invention also includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates, or faroates. The corticosteroids may optionally also be in the form of their hydrates.

Within the scope of the present invention, the term dopamine agonists, which is optionally used in conjunction with the compounds of formula 1, denotes compounds selected from among bromocriptine, cabergoline, α-dihydroergocryptine, lisuride, pergolide, pramipexole, roxindole, ropinirole, talipexole, terguride, and viozan. It is preferable within the scope of the present invention to use, as combination partners with the compounds of formula 1, dopamine agonists selected from among pramipexole, talipexole, and viozan, pramipexole being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of antiallergic agents which may be used according to the invention as a combination with the compounds of formula 1 include epinastine, cetirizine, azelastine, fexofenadine, levocabastine, loratadine, mizolastine, ketotifen, emedastine, dimethindene, clemastine, bamipine, dexchlorpheniramine, pheniramine, doxylamine, chlorphenoxamine, dimenhydrinate, diphenhydramine, promethazine, ebastine, desloratidine, and meclizine. Preferred antiallergic agents which may be used within the scope of the present invention in combination with the compounds of formula 1 according to the invention are selected from among epinastine, cetirizine, azelastine, fexofenadine, levocabastine, loratadine, ebastine, desloratidine, and mizolastine, epinastine and desloratidine being particularly preferred. Any reference to the abovementioned antiallergic agents also includes, within the scope of the present invention, a reference to any pharmacologically acceptable acid addition salts thereof which may exist.

The following are examples of PAF antagonists which may be used in conjunction with the compounds of formula 1 according to the invention:

(a) 4-(2-chlorophenyl)-9-methyl-2-[3(4-morpholinyl)-3-propanon-1-yl]-6H-thieno-[3,2-f][1,2,4]triazolo[4,3-a][1,4]diazepine, and (b) 6-(2-chlorophenyl)-8,9-dihydro-1-methyl-8-[(4-morpholinyl)carbonyl]4H,7H-cyclopenta-[4,5]thieno-[3,2-f][1,2,4]triazolo[4,3-a][1,4]diazepine.

Suitable preparations for administering the compounds of formula 1 include tablets, capsules, suppositories, solutions, etc.

Of particular importance according to the invention (particularly when treating asthma or COPD) is the administration of the compounds according to the invention by inhalation. The proportion of pharmaceutically active compound or compounds should be in the range from 0.05 to 90% by weight, preferably 0.1 to 50% by weight of the total composition. Suitable tablets may be obtained, for example, by mixing the active substance(s) with known excipients, for example inert diluents such as calcium carbonate, calcium phosphate, or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such asp-hydroxybenzoates.

Solutions are prepared in the usual way, e.g., with the addition of isotonic agents, preservatives such as p-hydroxybenzoates, or stabilizers such as alkali metal salts of ethylenediamine tetraacetic acid, optionally using emulsifiers and/or dispersants, whilst if water is used as the diluent, for example, optionally organic solvents is optionally used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as e.g., natural mineral powders (e.g., kaolins, clays, talc, chalk), synthetic mineral powders (e.g., highly dispersed silicic acid and silicates), sugars (e.g., cane sugar, lactose, and glucose), emulsifiers (e.g., lignin, spent sulfite liquors, methylcellulose, starch, and polyvinylpyrrolidone) and lubricants (e.g., magnesium stearate, talc, stearic acid, and sodium lauryl sulfate).

The preparations are administered by the usual methods, preferably by inhalation in the treatment of asthma or COPD. For oral administration the tablets may, of course, contain, apart from the abovementioned carriers, additives such as sodium citrate, calcium carbonate, and dicalcium phosphate together with various additives such as starch, preferably potato starch, gelatine, and the like. Moreover, lubricants such as magnesium stearate, sodium lauryl sulfate, and talc may be used at the same time for the tabletting process. In the case of aqueous suspensions the active substances may be combined with various flavor enhancers or colorings in addition to the excipients mentioned above.

The dosage of the compounds according to the invention is naturally greatly dependent on the route of administration and the complaint to be treated. When administered by inhalation the compounds of formula 1 are characterized by high efficacy even at doses in the $\mu$g range. The compounds of formula 1 can also be used effectively above the $\mu$g range. The dosage may then be in the gram range, for example. Particularly when administered by a method other than inhalation, the compounds according to the invention may be given in higher doses (in the range from 1 mg to 1000 mg, for example, although this does not imply any limitation).

The examples of formulations which follow illustrate the present invention without restricting its scope:

Examples of Pharmaceutical Formulations

| A. Tablets Containing 100 mg of Active Substance | |
|---|---|
| Component | Amount per tablet (mg) |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated, and dried. The granules, the remaining corn starch and the magnesium stearate are screened and mixed together. The mixture is compressed to produce tablets of suitable shape and size.

| B. Tablets Containing 80 mg of Active Substance | |
|---|---|
| Component | Amount per tablet (mg) |
| active substance | 80 |
| lactose | 55 |
| corn starch | 190 |
| microcrystalline cellulose | 35 |
| polyvinylpyrrolidone | 15 |
| sodium-carboxymethyl starch | 23 |
| magnesium stearate | 2 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C. Ampoules Containing 50 mg of Active Substance | |
|---|---|
| Component | Amount |
| active substance | 50.0 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

D. Metering Aerosol

| Component | Amount |
| --- | --- |
| active substance | 0.005 |
| sorbitan trioleate | 0.1 |
| monofluorotrichloromethane and difluorodichloromethane (2:3) | ad 100 |

The suspension is transferred into a conventional aerosol container with a metering valve. Preferably, 50 μl of suspension are delivered per spray. The active substance may also be metered in higher doses if desired (e.g., 0.02% by weight).

E. Solution

| Component | Amount (per 100 ml solution) |
| --- | --- |
| active substance | 333.3 mg |
| formoterol fumarate | 333.3 mg |
| benzalkonium chloride | 10.0 mg |
| EDTA | 50.0 mg |
| HCl (1 N) | ad pH 3.4 |

This solution may be prepared in the usual manner.

F. Powder for Inhalation

| Component | Amount |
| --- | --- |
| active substance | 6 μg |
| formoterol fumarate | 6 μg |
| lactose monohydrate | ad 25 mg |

The powder for inhalation is produced in the usual way by mixing the individual ingredients together.

G. Powder for Inhalation

| Component | Amount |
| --- | --- |
| active substance | 10 μg |
| lactose monohydrate | ad 5 mg |

The powder for inhalation is produced in the usual way by mixing the individual ingredients

We claim:

1. A compound of formula 1

1 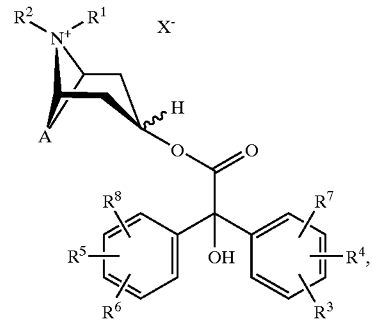 wherein:

A is a group selected from and $X^-$ is an anion with a single negative charge:

$R^1$ and $R^2$ are each independently a $C_1$–$C_4$-alkyl optionally substituted with hydroxy or halogen;

$R^3$ and $R^5$ are each independently fluorine, chlorine, or bromine; and $R^4$, $R^6$, $R^7$, and $R^8$ are each independently hydrogen, fluorine, chlorine, or bromine.

2. The compound of formula 1 according to claim 1, wherein:

A is

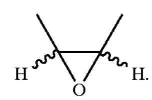

.

3. The compound of formula 1 according to claim 1, wherein:

$R^1$ and $R^2$ are each methyl;

$R^3$ and $R^5$ are each fluorine; and $R^4$, $R^6$, $R^7$, and $R^8$ are each independently hydrogen or fluorine.

4. A pharmaceutical composition comprising a compound of formula 1 according to claim 1 and a pharmaceutically acceptable excipient and/or carrier.

5. A pharmaceutical composition comprising a compound of formula 1 according to claim 2 and a pharmaceutically acceptable excipient and/or carrier.

6. A pharmaceutical composition comprising a compound of formula 1 according to claim 3 and a pharmaceutically acceptable excipient and/or carrier.

7. A method of treating COPD comprising administering to a host in need of such treatment a compound of formula 1 according to claim 1.

8. A method of treating COPD comprising administering to a host in need of such treatment a compound of formula 1 according to claim 2.

9. A method of treating COP comprising administering to a host in need of such treatment a compound of formula 1 according to claim 3.

10. A method of treating asthma, spasms in the gastrointestinal tract, or spasms in the urinary tract, administering to a host in need of such treatment a compound of formula 1 according to claim 1.

11. A method of treating asthma, spasms in the gastrointestinal tract, or spasms in the urinary tract, comprising administering to a host in need of such treatment a compound of formula 1 according to claim 2.

12. A method of treating asthma, spasms in the gastrointestinal tract, or spasms in the urinary tract, comprising administering to a host in need of such treatment a compound of formula 1 according to claim 3.

13. A compound of formula 4

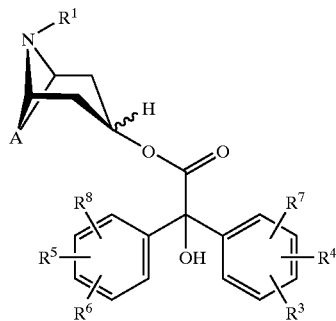

4 wherein:

A is a group selected from

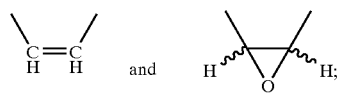

$R^1$ is a $C_1$–$C_4$-alkyl optionally substituted with hydroxy or halogen;

$R^3$ and $R^5$ are each independently fluorine, chlorine, or bromine; and $R^4$, $R^6$, $R^7$, and $R^8$ are each independently hydrogen, fluorine, chlorine, or bromine.

14. The compound of formula 4 according to claim 13, wherein:

$R^1$ is a group selected from the group consisting of methyl, ethyl, n-propyl, and isopropyl, each optionally substituted by hydroxy or fluorine.

15. The compound of formula 4 according to claim 13, wherein:

$R^1$ is methyl or ethyl.

16. The compound of formula 4 according to claim 15, wherein:

$R^1$ is methyl.

17. The compound of formula 4 according to claim 13, wherein:

$R^3$ and $R^5$ are each fluorine; and $R^4$, $R^6$, $R^7$, and $R^8$ are each independently hydrogen or fluorine.

* * * * *